(12) United States Patent
Pandey et al.

(10) Patent No.: US 8,987,463 B2
(45) Date of Patent: Mar. 24, 2015

(54) METHODS OF SYNTHESIZING FACTOR XA INHIBITORS

(71) Applicants: Millennium Pharmaceuticals, Inc., Cambridge, MA (US); Portola Pharmaceuticals, Inc., South San Francisco, CA (US)

(72) Inventors: Anjali Pandey, Fremont, CA (US); Emilia P. T. Leitao, Lisbon (PT); Jose Rato, Lisbon (PT); Zhiguo Jake Song, Edison, NJ (US)

(73) Assignees: Millennium Pharmaceuticals, Inc., Cambridge, MA (US); Portola Pharmaceuticals, Inc., South San Francisco, CA (US)

( * ) Notice: Subject to any disclaimer, the term of this patent is extended or adjusted under 35 U.S.C. 154(b) by 13 days.

(21) Appl. No.: 13/757,483

(22) Filed: Feb. 1, 2013

(65) Prior Publication Data

US 2013/0211094 A1   Aug. 15, 2013

Related U.S. Application Data

(62) Division of application No. 12/969,371, filed on Dec. 15, 2010, now Pat. No. 8,394,964.

(60) Provisional application No. 61/287,680, filed on Dec. 17, 2009.

(51) Int. Cl.
*C07D 213/75* (2006.01)

(52) U.S. Cl.
CPC .................................. *C07D 213/75* (2013.01)
USPC ....................................................... 546/309

(58) Field of Classification Search
None
See application file for complete search history.

(56) References Cited

U.S. PATENT DOCUMENTS

| | | | |
|---|---|---|---|
| 6,376,515 B2 | 4/2002 | Zhu |
| 6,835,739 B2 | 12/2004 | Zhu |
| 6,844,367 B1 | 1/2005 | Zhu |
| 7,022,695 B2 | 4/2006 | Zhu |
| 7,285,565 B2 | 10/2007 | Zhu |
| 7,312,235 B2 | 12/2007 | Zhu |
| 7,314,874 B2 | 1/2008 | Zhu |
| 7,342,013 B2 | 3/2008 | Zhu |
| 7,521,470 B2 | 4/2009 | Zhu |
| 7,598,276 B2 | 10/2009 | Grant |
| 7,696,352 B2 | 4/2010 | Zhu |
| 7,727,981 B2 | 6/2010 | Zhu |
| 7,727,982 B2 | 6/2010 | Zhu |
| 7,763,608 B2 | 7/2010 | Song |
| 7,767,697 B2 | 8/2010 | Song |
| 8,394,964 B2 | 3/2013 | Pandey et al. |
| 2003/0162690 A1 | 8/2003 | Zhu |
| 2008/0153876 A1 | 6/2008 | Sinha |
| 2008/0254036 A1 | 10/2008 | Sinha |
| 2008/0293704 A1 | 11/2008 | Jia |
| 2009/0298806 A1 | 12/2009 | Zhu |
| 2010/0063113 A1 | 3/2010 | Grant |
| 2010/0197929 A1 | 8/2010 | Scarborough |
| 2010/0234352 A1 | 9/2010 | Zhu |
| 2010/0249117 A1 | 9/2010 | Song |
| 2010/0298284 A1 | 11/2010 | Zhu |
| 2011/0152530 A1 | 6/2011 | Pandey |
| 2011/0160196 A1 | 6/2011 | Jia |
| 2011/0160250 A1 | 6/2011 | Pandey |
| 2011/0178135 A1 | 7/2011 | Pandey |

FOREIGN PATENT DOCUMENTS

| | | |
|---|---|---|
| EP | 1065200 | 1/2001 |
| JP | 2007-508308 | 4/2007 |
| WO | WO 99/47503 | 9/1999 |
| WO | WO 2004/083174 | 9/2004 |
| WO | WO 2005/034867 | 4/2005 |
| WO | WO 2008/057972 | 5/2008 |

OTHER PUBLICATIONS

U.S. Appl. No. 11/396,384, filed Mar. 30, 2006, Zhu.
U.S. Appl. No. 11/871,947, filed Oct. 12, 2007, Zhu.
U.S. Appl. No. 11/924,478, filed Oct. 25, 2007, Zhu.
International Search Report for PCT/US2010/060572, mailed Mar. 11, 2011, 3 pgs.
U.S. Appl. No. 11/924,481, filed Oct. 25, 2007, Zhu.
U.S. Appl. No. 11/969,758, filed Jan 4, 2008, Jia.

*Primary Examiner* — Zinna Northington Davis
(74) *Attorney, Agent, or Firm* — Sheppard Mullin Richter & Hampton LLP

(57) ABSTRACT

Described herein are novel methods of preparing a compound of Formula II or a pharmaceutically acceptable salt thereof. In some embodiments, the method is for preparing betrixaban or a pharmaceutically acceptable salt thereof. Also described are compositions comprising substantially pure betrixaban free base or salt thereof.

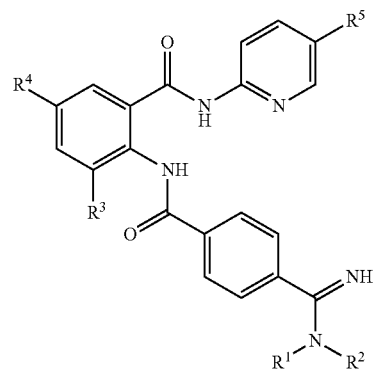

Formula II

5 Claims, 5 Drawing Sheets

METHODS OF SYNTHESIZING FACTOR XA INHIBITORS

CROSS REFERENCE TO RELATED APPLICATIONS

This application is a divisional of U.S. patent application Ser. No. 12/969,371 filed on Dec. 15, 2010, now U.S. Pat. No. 8,394,964, which claims the benefit under 35 U.S.C. §119(e) of U.S. Provisional Application Ser. No. 61/287,680 filed on Dec. 17, 2009, each of which is hereby incorporated by reference in its entirety.

BACKGROUND OF THE INVENTION

1. Field of the Invention

This invention is directed to methods for synthesizing factor Xa inhibitors as well as to the synthesis of intermediates and pharmaceutically acceptable salts thereof. Also described herein are compositions comprising substantially pure betrixaban free base or betrixaban maleate salt.

2. State of the Art

Factor Xa, a serine protease, plays an important role in the blood coagulation pathway. Direct inhibition of factor Xa has been considered to be an efficient anticoagulant strategy in the treatment of thrombotic diseases.

U.S. Pat. No. 6,376,515 B2 discloses a class of benzamide based compounds as specific factor Xa inhibitors. In particular, U.S. Pat. No. 6,376,515 B2 describes a compound identified as Example 206, which is also disclosed in U.S. Pat. No. 6,835,739 B2 as Example 206 and herein identified as betrixaban, which has the chemical formula of Formula I:

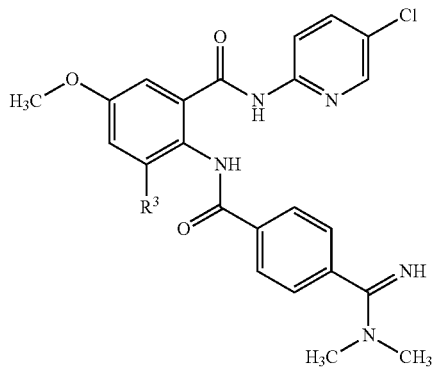

In light of the relevance of the benzamide compounds in treating thrombotic diseases, there exists a need in an efficient method of making the compounds and their intermediates.

SUMMARY OF THE INVENTION

This invention is directed to methods of preparing and recovering a compound of Formula II, for example betrixaban free base, or a salt thereof. The methods also include preparation of intermediates compounds of Formula II and recovering the same.

In one aspect, this invention is directed to a method of preparing a compound of Formula II or a salt thereof,

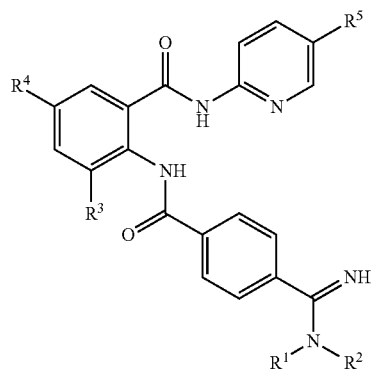

comprising
contacting a compound of Formula II-A:

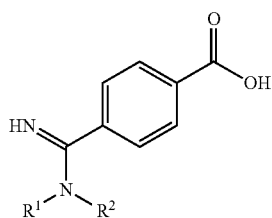

with a compound of Formula II-B:

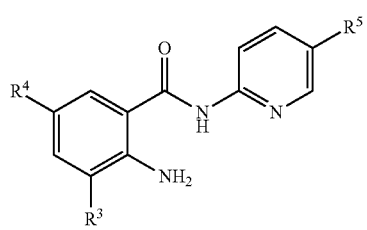

under reaction conditions to form the compound of Formula II or the salt thereof
wherein
$R^1$ and $R^2$ are independently $C_{1-6}$ alkyl;
$R^3$ and $R^4$ are independently selected from the group consisting of hydrogen, fluoro, chloro, bromo, and methoxy; and
$R^5$ is selected from the group consisting of fluoro, chloro, bromo, and methoxy.

In one embodiment, this invention provides a method of preparing betrixaban or a salt thereof, comprising:
contacting a compound of Formula A:

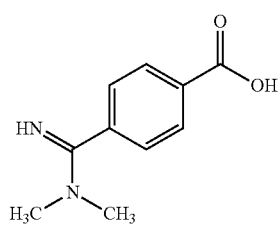

with a compound of Formula B:

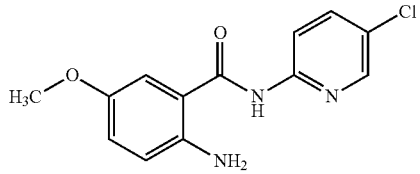

under reaction conditions to form betrixaban or the salt thereof.

In some embodiments, the method further comprises recovering the free base of betrixaban by adding base.

In another embodiment, this invention provides a method of preparing betrixaban or a salt thereof:

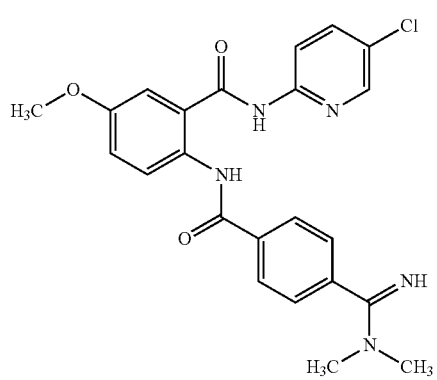

comprising:

a) contacting a compound of Formula D:

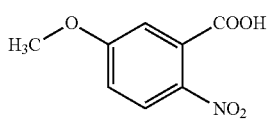

with a compound of Formula E:

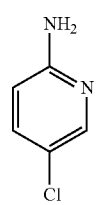

under reaction conditions optionally comprising acetonitrile as a solvent to form a compound of Formula C:

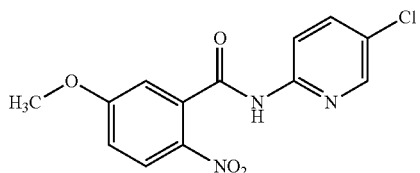

b) exposing the compound of Formula C to reaction conditions to form a compound of Formula B:

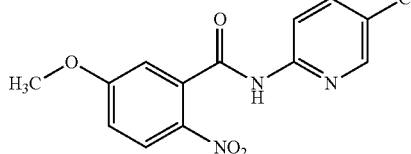

c) contacting the compound of Formula B with a compound of Formula A:

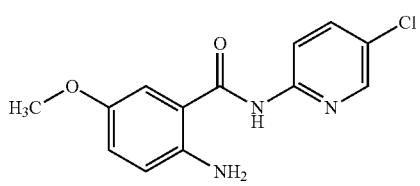

under reaction conditions to form betrixaban or the salt thereof.

In some embodiments, the method further comprises contacting the compound of Formula II or the salt thereof with an acid to give a pharmaceutically acceptable salt of the compound of Formula II. In some embodiments, the method further comprises recovering the pharmaceutically acceptable salt of the compound of Formula II. In one embodiment, the pharmaceutically acceptable salt of betrixaban is a maleate salt. In another embodiment, the method comprises contacting betrixaban or a salt thereof with at least a molar equivalent of maleic acid in a solvent mixture of $C_{1-4}$ alkanol and water at a temperature of between 10° C. and 40° C. under reaction conditions to form the maleate salt of betrixaban.

In another embodiment, this invention provides a method of preparing betrixaban or a pharmaceutically acceptable salt thereof on a large scale, such as the gram or kilogram scale.

In yet another embodiment is provided substantially pure betrixaban free base or betrixaban maleate salt. In some embodiments, the invention is directed to compositions comprising substantially pure betrixaban free base or betrixaban maleate salt. In one embodiment, the composition comprises at least 99.3% betrixaban free base. In yet another embodiment, the composition comprising at least 99.7% betrixaban maleate salt. Also provided is a composition comprising betrixaban free base or maleate salt that is substantially free of Compound L and/or Compound M:

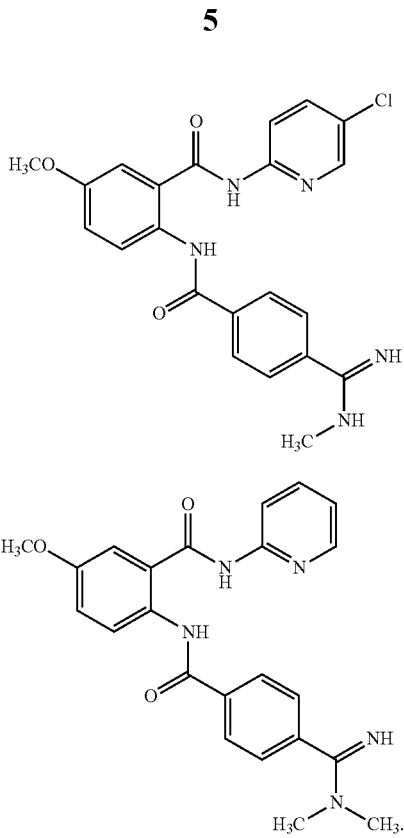

In still another embodiment, this invention provides a composition comprising at least 99.3% betrixaban free base, which composition is obtainable by (1) contacting a compound of Formula A

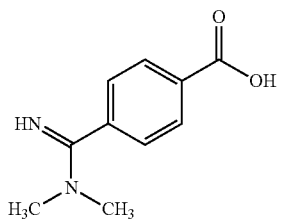

with a compound of Formula B

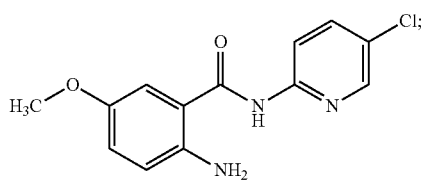

under reaction conditions to form betrixaban free base;
(2) recovering betrixaban free base obtained in (1) with a purity of equal to or greater than 99.3%.

In still another embodiment this invention provides a composition comprising at least 99.7% betrixaban maleate salt, which composition is obtainable by (1) contacting a compound of Formula A

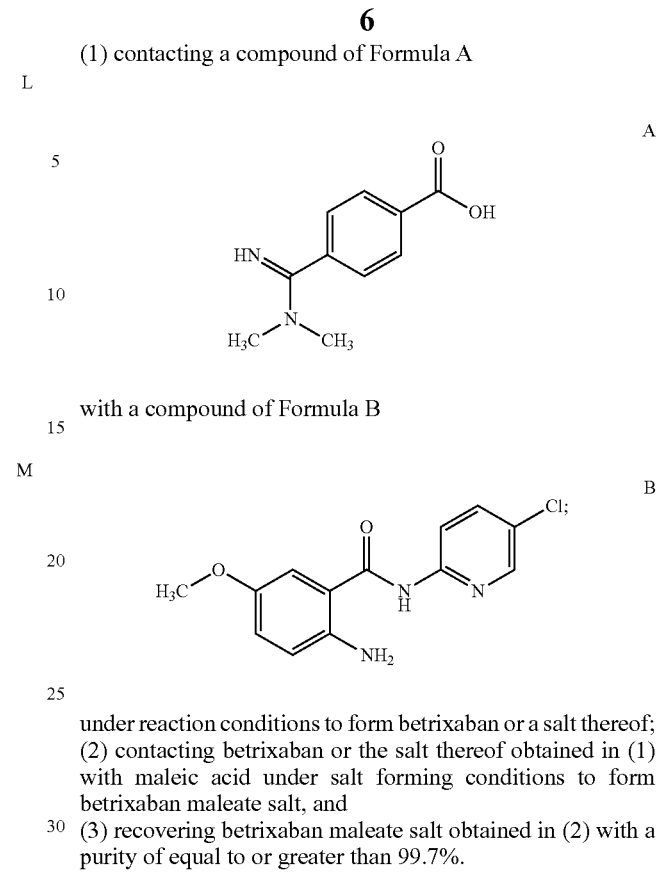

with a compound of Formula B under reaction conditions to form betrixaban or a salt thereof;
(2) contacting betrixaban or the salt thereof obtained in (1) with maleic acid under salt forming conditions to form betrixaban maleate salt, and
(3) recovering betrixaban maleate salt obtained in (2) with a purity of equal to or greater than 99.7%.

It is contemplated that the purity is consistent even when the above methods are performed on larger scales.

DETAILED DESCRIPTION OF THE INVENTION

Figure 1:
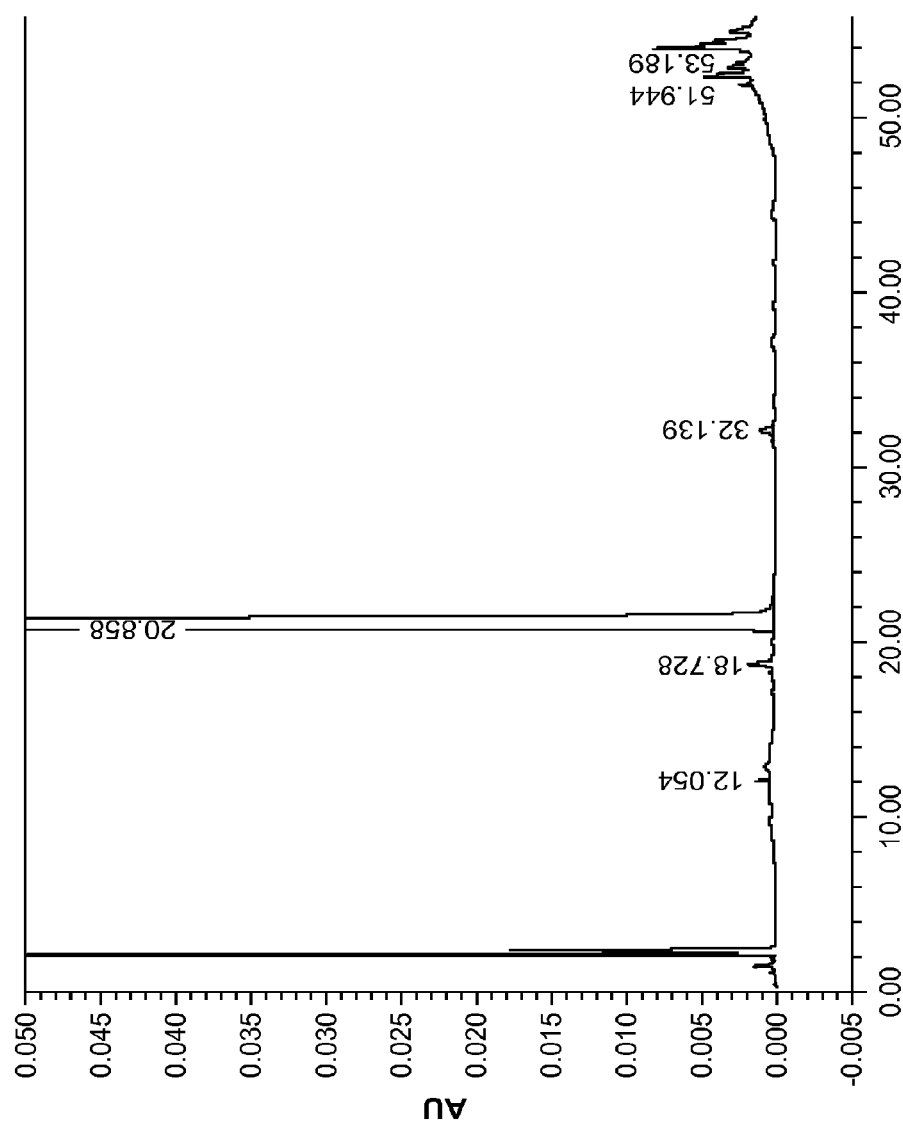
FIG. 1 provides a high performance liquid chromatography (HPLC) chromatogram of betrixaban maleate salt obtained by the method described in Scheme 1.

As discussed in U.S. Pat. No. 6,376,515 which is a continuation-in-part of U.S. Pat. No. 6,844,367 (the '367 patent), a class a benzamide compounds, including betrixaban, are potent Xa inhibitors. The present invention involves a novel synthesis of compounds of Formula II, for example betrixaban. The present invention also involves conversion of the compound of Formula II to a pharmaceutically acceptable salt thereof, for example, a maleate salt of betrixaban. The maleate salt of betrixaban has excellent crystallinity, thermal and hydrolytic stability, and purity. The present invention involves the synthesis of a compound of Formula II or a pharmaceutically acceptable salt on a gram as well as a kilogram scale.

I. Definitions

As used in the specification and claims, the singular form "a", "an" and "the" include plural references unless the context clearly dictates otherwise.

As used herein, the term "comprising" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude elements that do not materially alter the novel characteristics of the claimed invention. "Consisting of" shall mean excluding more than trace amount of other ingredients and substantial method steps recited. Embodiments defined by each of these transition terms are within the scope of this invention.

As used herein, "betrixaban" refers to the chemical compound which has the chemical formula of Formula I:

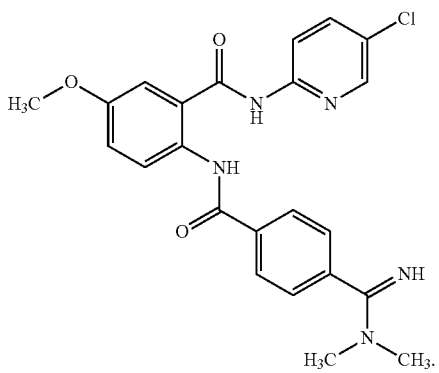

I

In some embodiments, betrixaban is referred to as the "free base" meaning that compound is able to accept one or more protons or donate one or more pairs of electrons. In other words, the amine groups are unprotonated.

As used herein, the term "$C_{1-4}$ alkanol" refers to monovalent saturated aliphatic hydrocarbyl compounds having from 1 to 4 carbon atoms and having one of the hydrogen atoms substituted with a hydroxy (OH) group. Examples of $C_{1-4}$ alkanol include methanol, ethanol, n-propanol, isopropanol, n-butanol, isobutanol, sec-butanol, and t-butanol.

As used herein, the term "$C_{1-6}$ alkyl" refers to monovalent saturated aliphatic hydrocarbyl groups having from 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—) and n-pentyl ($CH_3CH_2CH_2CH_2CH_2$—).

As used herein, the term "solvent" refers to a liquid that dissolves a solid, liquid, or gaseous solute to form a solution. Common solvents are well known in the art and include but are not limited to, water; saturated aliphatic hydrocarbons, such as pentane, hexane, heptanes, and other light petroleum; aromatic hydrocarbons, such as benzene, toluene, xylene, etc.; halogenated hydrocarbons, such as dichloromethane, chloroform, carbon tetrachloride, etc.; aliphatic alcohols, such as methanol, ethanol, propanol, etc.; ethers, such as diethyl ether, dipropyl ether, dibutyl ether, tetrahydrofuran, dioxane, etc.; ketones, such as acetone, ethyl methyl ketone, etc.; esters, such as methyl acetate, ethyl acetate, etc.; nitrogen-containing solvents, such as dimethylacetamide, formamide, N,N-dimethylformamide, acetonitrile, pyridine, N-methylpyrrolidone, quinoline, nitrobenzene, etc.; sulfur-containing solvents, such as carbon disulfide, dimethyl sulfoxide, sulfolane, etc.; phosphorus-containing solvents, such as hexamethylphosphoric triamide, etc. The term solvent includes a combination of two or more solvents unless clearly indicated otherwise. A particular choice of a suitable solvent will depend on many factors, including the nature of the solvent and the solute to be dissolved and the intended purpose, for example, what chemical reactions will occur in the solution, and is generally known in the art.

As used herein, the term "contacting" refers to bringing two or more chemical molecules to close proximity so that a reaction between the two or more chemical molecules can occur. For example, contacting may comprise mixing and optionally continuously mixing the chemicals. Contacting may be done by fully or partially dissolving or suspending two or more chemicals in one or more solvents, mixing of a chemical in a solvent with another chemical in solid and/or gas phase or being attached on a solid support, such as a resin, or mixing two or more chemicals in gas or solid phase and/or on a solid support, that are generally known to those skilled in the art.

As used herein, the term "reaction conditions" refers to the details under which a chemical reaction proceeds. Examples of reaction conditions include, but are not limited to, one or more of the following: reaction temperature, solvent, pH, pressure, reaction time, mole ratio of reactants, the presence of a base or acid, or catalyst, etc. Reaction conditions may be named after the particular chemical reaction in which the conditions are employed, such as, coupling conditions, hydrogenation conditions, acylation conditions, reduction conditions, salt forming conditions, etc. Reaction conditions for known reactions are generally known to those skilled in the art.

The term "acid" is intended to refer to a chemical species that can either donate a proton or accept a pair of electrons from another species. Examples of acids include organic acids, such as carboxylic acids (e.g. maleic acid, lactic acid, acetic acid, formic acid, citric acid, oxalic acid, uric acid, etc.) and sulfonic acids (e.g., methanesulfonic acid, p-toluenesulfonic acid); mineral acids (e.g. hydrochloric acid, nitric acid, phosphoric acid, sulfuric acid, boric acid, hydrofluoric acid, hydrobromic acid); and Lewis acids. The term "Lewis acid" is used herein refers to an electron deficient species that is capable of accepting a pair of electrons. Examples of Lewis acids that can be used in the present invention are cations of metals and their complexes, where such metals include magnesium, calcium, aluminum, zinc, titanium, chromium, copper, boron, tin, mercury, iron, manganese, cadmium, gallium and barium. The metal complex may include one or more ions, including, but not limited to, hydroxides, alkyls, alkoxides, halides and organic acid ligands, such as acetates.

As used herein, the term "base" generally refers to chemical compounds that can accept hydrogen ions. The term "inorganic base" refers to an inorganic compound that can act as a base. Examples of inorganic base include, but are not limited to, sodium carbonate, potassium hydroxide (KOH), barium hydroxide ($Ba(OH)_2$), cesium hydroxide (CsOH), sodium hydroxide (NaOH), strontium hydroxide ($Sr(OH)_2$), calcium hydroxide ($Ca(OH)_2$), lithium hydroxide (LiOH), rubidium hydroxide (RbOH), and magnesium hydroxide ($Mg(OH)_2$). The term "organic base" refers to an organic compound that can act as a base. Examples of inorganic base include, but are not limited to, triethylamine, N-methylmorpholine, diisopropylethylamine, pyridine and 4-dimethylaminopyridine (DMAP).

As used herein, the term "salt formation conditions" or "salt forming conditions" generally refers to conditions used to form a salt between, for example, a compound having a basic group, such as betrixaban with an organic or inorganic acid. Salt forming conditions may include mixing the molecule having the basic group and the acid in a solvent or a mixture of solvents for a period of time under a certain temperature, which would be generally known to a person skilled in the art. Alternatively, the compound can be passed over an ion exchange resin to form the desired salt or one salt form of the product can be converted into another using the same general process. The first salt can then be converted to a second salt such as a maleate salt. Salt forming conditions may also be conditions where the acid is a by-product of a reaction forming the compound whose salt is formed.

As used herein, the term "coupling conditions" generally refers to conditions used in coupling reactions where two chemical entities are connected to form one chemical entity via a coupling reagent. In some cases, a coupling reaction refers to the reaction connecting a compound bearing a carboxylic acid group to a compound bearing an amino group to form a compound having an amide bond, which may be referred to as "amide coupling reaction". Coupling conditions generally include a coupling reagent, such as an amide coupling reagent in an amide coupling reaction. Common amide coupling reagents also include, but are not limited to, phosphorous oxychloride ($POCl_3$), 2-propanephosphonic acid anhydride (T3P), carbonyldiimidazole (CDI), 2-chloro-4,6-dimethoxy-1,2,5-triazine (CDMT), carbodiimides such as N—N'-dicyclohexylcarbodiimide (DCC), N,N'-diisopropylcarbodiimide (DIC), and 1-ethyl-3-(3'-dimethylaminopropyl)carbodiimide or N-(3-dimethylaminopropyl)-N'-ethylcarbodiimide (EDC). The carbodiimides may be used in conjunction with additives such as dimethylaminopyridine (DMAP) or 1-hydroxybenzotriazole (HOBt). Amide coupling reagents also include amininum and phosphonium based reagents, such as N-[(dimethylamino)-1H-1,2,3-triazolo[4,5-b]pyridine-1-ylmethylene]-N-methylmethanaminium hexafluorophosphate N-oxide (HATU), N-[(1H-benzotriazol-1-yl)(dimethylamino)methylene]-N-methylmethanaminium hexafluorophosphate N-oxide (HBTU) and benzotriazol-1-yl-N-oxy-tris(pyrrolidino)phosphonium hexafluorophosphate (PyBOP). Amide coupling conditions may include a solvent such as dimethylformamide (DMF), tetrahydrofuran (THF), dichloromethane (DCM), acetone, dimethylacetamide (DMA), ethyl acetate (EtOAc), acetonitrile or mixtures thereof, and may also include an organic base such as pyridine, triethylamine (TEA), diisopropylethylamine (DIEA), dimethylaminopyridine (DMAP), N-methylmorpholine (NMM) or mixtures thereof. Coupling conditions may include a temperature of between −10° C. to room temperature.

As used herein, the term "hydrogenation conditions" generally refers to conditions used in reactions where hydrogen gas reacts with a compound, for example, a nitro compound, to form a new compound, such as an amino compound. Hydrogenation conditions may include hydrogen gas, a catalyst such as palladium, platinum, or sulfided platinum, a solvent or a mixture of solvents and a suitable temperature.

As used herein, the term "catalyst" refers to a chemical substance which, when used in certain chemical reactions, increases the rate of the chemical reaction or makes the chemical reactions proceed in a practical manner. A catalyst itself is not consumed by the reaction. Many suitable catalysts are generally known for many reactions. For example, catalysts for a hydrogenation reaction include are not limited to platinum, palladium, rhodium, iron and ruthenium, or compounds or compositions thereof, for example, palladium deposited carbon, barium sulfate or calcium carbonate. One example of catalysts used in a hydrogenation reaction is sulfide platinum on activated carbon. New catalysts for known reactions or for new reactions have been emerging with the advance of the chemical science. As used herein, all suitable catalysts are encompassed unless specifically indicated otherwise. In some embodiments, the catalyst is sulfided platinum on carbon.

As used herein, the term "pharmaceutically acceptable salt" refers to a salt of a compound that is derived from a variety of physiologically acceptable organic and inorganic counter ions. Such counter ions are well known in the art and include, by way of example only, sodium, potassium, calcium, magnesium, aluminum, lithium and ammonium, for example tetraalkylammonium, and the like when the molecule contains an acidic functionality; and when the molecule contains a basic functionality, salts of organic or inorganic acids, such as hydrochloride, sulfate, phosphate, diphosphate, nitrate hydrobromide, tartrate, mesylate, acetate, malate, maleate, fumarate, tartrate, succinate, citrate, lactate, pamoate, salicylate, stearate, methanesulfonate, p-toluenesulfonate, and oxalate, and the like. Suitable pharmaceutically acceptable salts also include those listed in Remington's Pharmaceutical Sciences, 17th Edition, pg. 1418 (1985) and P. Heinrich Stahl, Camille G. Wermuth (Eds.), Handbook of Pharmaceutical Salts Properties, Selection, and Use; 2002. Examples of acid addition salts include those formed from acids such as hydroiodic, phosphoric, metaphosphoric, nitric and sulfuric acids, and with organic acids, such as alginic, ascorbic, anthranilic, benzoic, camphorsulfuric, citric, embonic (pamoic), ethanesulfonic, formic, fumaric, furoic, galacturonic, gentisic, gluconic, glucuronic, glutamic, glycolic, isonicotinic, isothionic, lactic, malic, mandelic, methanesulfonic, mucic, pantothenic, phenylacetic, propionic, saccharic, salicylic, stearic, succinic, sulfinilic, trifluoroacetic and arylsulfonic for example benzenesulfonic and p-toluenesulfonic acids. Examples of base addition salts formed with alkali metals and alkaline earth metals and organic bases include chloroprocaine, choline, N,N-dibenzylethylenediamine, diethanolamine, ethylenediamine, lysine, meglumaine (N-methylglucamine), and procaine, as well as internally formed salts. Salts having a non-physiologically acceptable anion or cation are within the scope of the invention as useful intermediates for the preparation of physiologically acceptable salts and/or for use in non-therapeutic, for example, in vitro, situations.

The term "obtainable" means that a composition of matter can be obtained by a particular method recited but may also be obtained by other method(s) not recited.

The term "substantially pure" refers to betrixaban free base or maleate salt that is at least about 99.3% pure, or 99.5% pure, or 99.7% pure, or 99.9% pure, or is 100% pure. Purity can be measured by any appropriate method, such as for example, column chromatography, HPLC analysis, etc. In some embodiments, the term "substantially pure" refers to compositions that are substantially free of side products, such as, by way of example only, side products having the chemical formula L and M:

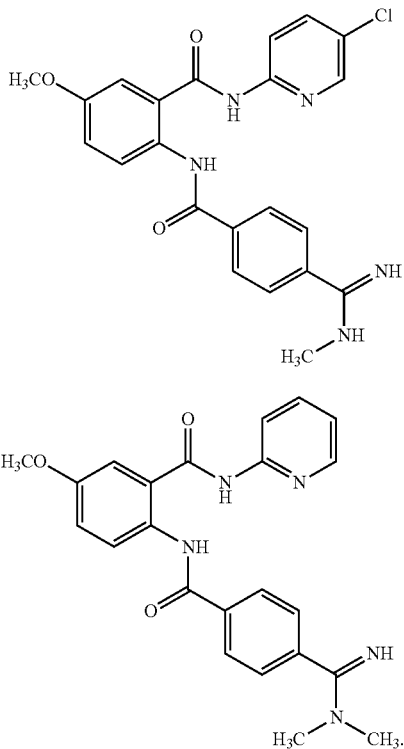

The term "substantially free" when used before a compound means that a composition comprises less than 0.7%, or less than 0.15%, or less than 0.1%, or less than 0.04%, or less than 0.03% of the compound.

It is to be understood that when a value is recited for a condition or a yield, the value may vary within a reasonable range, such as ±10%, ±5%, and ±1%. Similarly, the term "about" when used before a numerical value indicates that the value may vary within reasonable range, such as ±10%, ±5%, and ±1%.

II. Synthetic Methods

This invention is directed to methods of preparing a compound of Formula II, for example betrixaban, or a pharmaceutically acceptable salt of the compound of Formula II, and intermediates thereof. The methods also include recovery of the products.

In one aspect, this invention is directed to a method of preparing a compound of Formula II or a salt thereof,

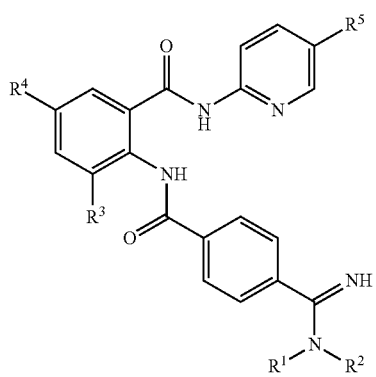

comprising
contacting a compound of Formula II-A:

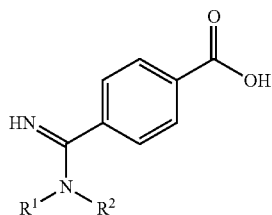

with a compound of Formula II-B:

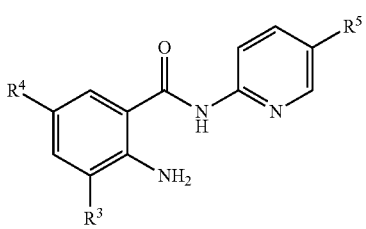

under reaction conditions to form the compound of Formula II or the salt thereof;
wherein
$R^1$ and $R^2$ are independently $C_{1-6}$ alkyl;
$R^3$ and $R^4$ are independently selected from the group consisting of hydrogen, fluoro, chloro, bromo, and methoxy; and
$R^5$ is selected from the group consisting of fluoro, chloro, bromo, and methoxy.

In some embodiments, $R^1$ and $R^2$ are the same $C_{1-6}$ alkyl. In some embodiments, $R^1$ and $R^2$ are both methyl.

In some embodiments, one of $R^3$ and $R^4$ is hydrogen, the other of $R^3$ and $R^4$ is selected from the group consisting of hydrogen, fluoro, chloro, bromo, and methoxy. In some embodiments, $R^3$ is hydrogen, and $R^4$ is selected from the group consisting of hydrogen, fluoro, chloro, bromo, and methoxy. In some embodiments, $R^3$ is hydrogen and $R^4$ is methoxy.

In some embodiments, $R^5$ is chloro or bromo. In some embodiments, $R^5$ is chloro.

In some embodiments, the reaction conditions comprise an amide coupling reagent. In some embodiments, the amide coupling reagent is selected from the group consisting of 2-propanephosphonic acid anhydride (T3P), carbonyldiimidazole (CDI), 2-chloro-4,6-dimethoxy-1,3,5-triazine (CDMT), N,N'-dicyclohexyl-carbodiimide (DCC), N,N'-diisopropylcarbodiimide (DIC), N-(3-dimethylaminopropyl)-N'-ethylcarbodiimide (EDC), and combinations thereof, optionally in combination with hydroxybenzotriazole (HOBt). In some embodiments, the coupling agent is selected from the group consisting of N,N'-dicyclohexyl-carbodiimide (DCC), N,N'-diisopropylcarbodiimide (DIC), and N-(3-dimethylaminopropyl)-N'-ethylcarbodiimide (EDC), optionally in combination with hydroxybenzotriazole (HOBt). In some embodiments, the coupling agent is N-(3-dimethylaminopropyl)-N'-ethylcarbodiimide and is in combination with hydroxybenzotriazole. In some embodiments, EDC is in the form of N-(3-dimethylaminopropyl)-N'-ethylcarbodiimide hydrochloride (EDC.HCl). In some embodiments, the coupling agent is EDC.HCl and is in combination with hydroxybenzotriazole. In some embodiments, the coupling agent is EDC.HCl and is in combination with HCl, for example, about one equivalent of HCl.

In some embodiments, the reaction conditions comprise a solvent. The solvent may be selected from the group consisting of dimethylformamide (DMF), ethyl acetate (EtOAc), dichloromethane (DCM), dimethylacetamide (DMA), acetone, N-methylpyrrolidone (NMP), acetonitrile, tetrahydrofuran (THF), and mixtures thereof. Other suitable solvent may also be used alone or in combination with the solvents listed above. In some embodiments, the reaction conditions comprise dimethylformamide and/or dimethylacetamide as a solvent.

In some embodiments, the reaction conditions of forming a compound of Formula II or a salt thereof further comprise a suitable base. In some embodiments, the base is selected from the group consisting of N-methylmorpholine (NMM), triethylamine, diisopropylethylamine (DIEA) and 4-dimethylaminopyridine (DMAP), and combinations thereof.

In some embodiments, the method is performed at a temperature of between about 0° C. and about 30° C. In some embodiments, the compound of Formula II or salts thereof, including betrixaban and salts thereof, is afforded in a yield of at least 65%. In some embodiments, compound of Formula II or salts thereof is afforded in a yield of at least 75%.

Generally, Compound II-A and Compound II-B have the same molar equivalents or one of Compound II-A or Compound II-B is in excess of the other compound. In some embodiments, Compound II-A is about 1 to 2 equivalents of Compound II-B, or 1 to 1.5 equivalents, or 1 to 1.2 equivalents of Compound II-B, or 1 to 1.1 equivalents of Compound II-B. In some embodiments, the coupling agent and optional HOBt, if present, are about 1 to 2 equivalents of Compound II-B, or 1 to 1.5 equivalents of Compound II-B, or 1 to 1.2 equivalents of Compound II-B.

In some embodiments, the free base of Compound II, for example, betrixaban, may be recovered after the coupling step by adding a sufficient amount of base, such as, e.g. sodium carbonate. In some embodiments, at least one molar equivalent of the base is added. In some embodiments, the base is added in excess, such as for example, at least about a 2 molar excess or about 3 molar excess. In some instances the base can be added while the batch is being cooled any where from about 25° C. to about 35° C. Optionally, water may be added. The resulting free base can be obtained by filtering and then optionally washing with water and acetone.

In some embodiments, this invention provides a method of preparing of a compound for Formula II, betrixaban, free base or a salt thereof from a compound of Formula II-A on a kilogram scale.

In some embodiments, the compound of Formula II-A is prepared by exposing a compound of Formula II-G:

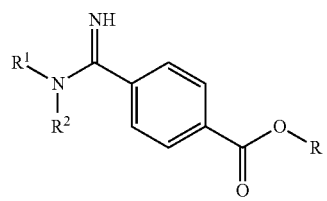

II-G to reaction conditions to form the compound of Formula II-A; wherein $R^1$ and $R^2$ are as previously defined and R is $C_{1-6}$ alkyl or benzyl.

In some embodiments, R is methyl or ethyl. In some embodiments, the reaction conditions comprise hydrolysis conditions, for example a base, such as lithium hydroxide (LiOH), sodium hydroxide (NaOH), or potassium hydroxide (KOH), water and an optional co-solvent such as THF, acetonitrile, methanol, ethanol, or other suitable solvents. In some embodiments, R is tert-butyl. In some embodiments, the reaction conditions comprise an acid, such as hydrochloric acid (HCl) or trifluoroacetic acid (TFA), and a suitable solvent. In some embodiments, R is benzyl. In some embodiments, the reaction conditions comprise hydrogen gas in the presence of a catalyst, such as palladium on carbon. Other suitable conditions of transforming the compound of Formula II-G to the compound of Formula II-A are generally known in the art and may also be used.

In some embodiments, the compound of Formula II-G is prepared by exposing the compound of Formula H:

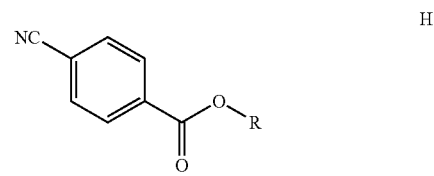

H to reaction conditions to form the compound of Formula II-G; where R is $C_{1-6}$ alkyl or benzyl.

In some embodiments, the reaction conditions comprise an amine $NHR^1R^2$, wherein $R^1$ and $R^2$ are as defined previously, $LiR^6$ (wherein $R^6$ is $C_{1-6}$ alkyl) and a suitable solvent. In some embodiments, $LiR^6$ is hexyllithium. In some embodiments, the solvent is a combination of tetrahydrofuran and hexane.

In some embodiments, reaction conditions of forming the compound of Formula G comprise:

(a) contacting the compound of Formula H with an alcohol, such as methanol or ethanol, in the presence of an acid, such as HCl, preferably at 0° C. to room temperature;

(b) contacting the intermediate obtained from step (a) with $HNR^1R^2$ to form the compound of Formula II-G, preferably under refluxing conditions.

Other suitable conditions of converting a cyano group (—CN) to a dialkylamidine group (—C(=NH)$NR^1R^2$) are generally known in the art.

Compound H may be obtained from 4-cyanobenzoic acid which is commercially available from commonly known ester formation reactions.

In some embodiments, the compound of Formula II-B is prepared by exposing the compound of Formula II-C:

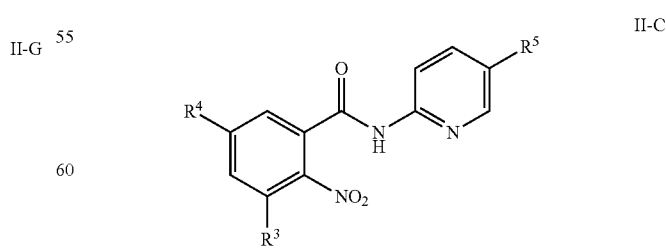

II-C to reduction conditions to form the compound of Formula II-B; where $R^3$, $R^4$, and $R^5$ are as defined herein.

In some embodiments, the reduction conditions comprise hydrogen gas in the presence of a catalyst, such as palladium on carbon. In some embodiments, the catalyst is sulfided 5% platinum on carbon. In some embodiments, the reaction conditions comprise a temperature of between 19° C. and 31° C., or between 21 to 31° C., or between 21 to 28° C., and a pressure of hydrogen from 20 to 40 psi, preferably 30 psi. In some embodiments, the reaction conditions comprise a solvent selected from the group consisting of methylene chloride, ethanol, methanol, and ethyl acetate. In some embodiments, the conditions comprise methylene chloride as a solvent. In some embodiments, the compound of Formula II-B is afforded in a yield of at least 80%. In some embodiments, the compound of Formula II-B is afforded in a yield of at least 85%.

In some embodiments, the compound of formula II-C is prepared by contacting a compound of Formula II-D:

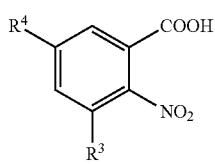

II-D with a compound of Formula II-E:

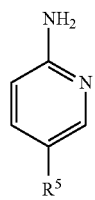

II-E under reaction conditions to form the compound of Formula II-C;

where $R^3$, $R^4$, and $R^5$ are as defined herein.

In some embodiments, this invention provides a method of preparing betrixaban which is of Formula I, or a salt thereof:

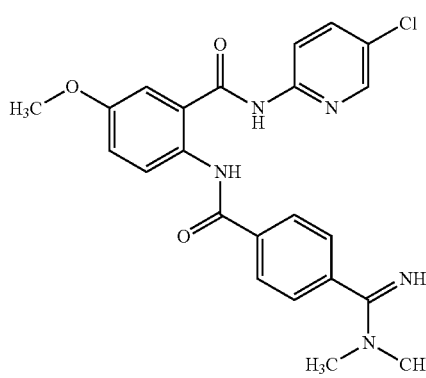

I comprising:

contacting a compound of Formula A:

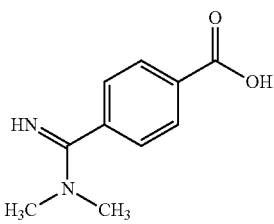

A with a compound of Formula B:

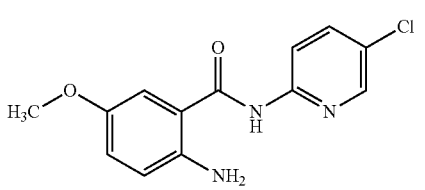

B under coupling conditions to form betrixaban or the salt thereof.

In some embodiments, the coupling conditions comprise an amide coupling reagent. In some embodiments, the amide coupling reagent is selected from the group consisting of 2-propanephosphonic acid anhydride (T3P), carbonyldiimidazole (CDI), 2-chloro-4,6-dimethoxy-1,3,5-triazine (CDMT), N,N'-dicyclohexyl-carbodiimide (DCC), N,N'-diisopropylcarbodiimide (DIC), N-(3-dimethylaminopropyl)-N'-ethylcarbodiimide (EDC), and combinations thereof, optionally in combination with hydroxybenzotriazole (HOBt). In some embodiments, the coupling agent is selected from the group consisting of N,N'-dicyclohexyl-carbodiimide (DCC), N,N'-diisopropylcarbodiimide (DIC), and N-(3-dimethylaminopropyl)-N'-ethylcarbodiimide (EDC), optionally in combination with hydroxybenzotriazole (HOBt). In some embodiments, the coupling agent is ethylcarbodiimide in combination with hydroxybenzotriazole. In some embodiments, EDC is in the form of ethylcarbodiimide hydrochloride (EDC.HCl). In some embodiments, the coupling agent is EDC.HCl and is in combination with HCl, for example, about one equivalent of HCl.

In some embodiments, the coupling conditions comprise a solvent, such as dimethylformamide (DMF), ethyl acetate (EtOAc), dichloromethane (DCM), dimethylacetamide (DMA), acetone, acetonitrile, tetrahydrofuran (THF), and mixtures thereof. Other suitable solvent may also be used alone or in combination with any of the above solvents. In some embodiments, the reaction conditions comprise dimethylformamide and/or dimethylacetamide as a solvent.

In some embodiments, the coupling conditions of forming betrixaban or a salt thereof further comprises a suitable base. In some embodiments, the base is selected from the group consisting of N-methylmorpholine (NMM), DIEA, triethylamine and 4-dimethylaminopyridine (DMAP), and combinations thereof.

In some embodiments, the free base of betrixaban may be recovered after the coupling step by adding a sufficient amount of base, such as, e.g. sodium carbonate. In some embodiments, the base is added in excess, such as for example, at least about a 2 molar excess or about 3 molar excess. In some instances the base can be added while the batch is being cooled any where from about 25° C. to about 35° C. Optionally, water may be added. The resulting free base can be obtained by filtering and then optionally washing with water and acetone.

In some embodiments, the method is performed between about 0° C. and about 30° C. In some embodiments, betrixaban or salt thereof is afforded in a yield of at least 65%. In some embodiments, betrixaban or salt thereof is afforded in a yield of at least 75%.

Generally, Compound A and Compound B have the same molar equivalents or one of Compound A or Compound B is in excess of the other compound. In some embodiments, Compound A is about 1 to 2 equivalents of Compound B, or 1 to 1.5 equivalents, or 1 to 1.1 equivalents of Compound B. In some embodiments, the coupling agent and optional HOBt, if present, are about 1 to 2 equivalents of Compound B, or 1 to 1.5 equivalents of Compound B, or 1 to 1.2 equivalents of Compound B.

In some embodiments, this invention provides a method of preparing betrixaban free base or a salt thereof from a compound of Formula A on a kilogram scale.

In some embodiments, the compound of Formula A is prepared by exposing a compound of Formula G:

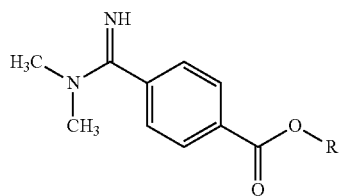

G to reaction conditions to form the compound of Formula A; wherein R is $C_{1-6}$ alkyl or benzyl.

In some embodiments, R is methyl or ethyl. In some embodiments, the reaction conditions comprise hydrolysis conditions, for example an inorganic base, such as LiOH, NaOH, or KOH, water and an optional co-solvent such as THF, acetonitrile, alcohol, or other suitable solvents. In some embodiments, R is tert-butyl. In some embodiments, the reaction conditions comprise an acid, such as hydrochloric acid or trifluoroacetic acid and a suitable solvent. In some embodiments, R is benzyl. In some embodiments, the reaction conditions comprise hydrogen gas in the presence of a catalyst, such as palladium on carbon. Other suitable conditions of transforming the compound of Formula G to the compound of Formula A may also be used.

In some embodiments, the compound of Formula G is prepared by exposing the compound of Formula H:

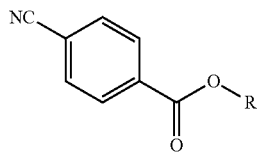

H to reaction conditions to form the compound of Formula G; where R is $C_{1-6}$ alkyl or benzyl.

In some embodiments, the reaction conditions comprise dimethylamine, $LiR^6$ (wherein $R^6$ is $C_{1-6}$ alkyl) and a solvent.

In some embodiments, $LiR^6$ is hexyllithium. In some embodiments, the solvent is a combination of tetrahydrofuran and hexane.

In some embodiments, reaction conditions of forming the compound of Formula G comprise:

(a) contacting the compound of Formula H with an alcohol, such as methanol or ethanol, in the presence of an acid, such as HCl, preferably at a temperature of between about 0° C. to room temperature;

(b) contacting the intermediate obtained from step (a) with dimethylamine to form the compound of Formula G, preferably under refluxing conditions.

Other suitable conditions of transforming a cyano group (—CN) to a dimethylamidine group (—C(=NH)N(CH$_3$)$_2$) are generally known in the art and may be used.

In some embodiments, the compound of Formula B is prepared by exposing the compound of Formula C:

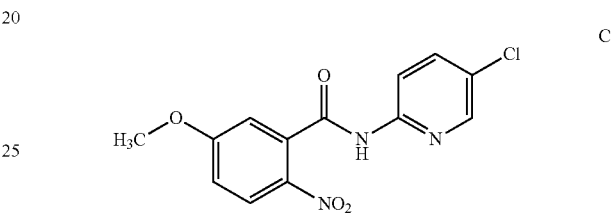

C to reduction conditions to form the compound of Formula B.

In some embodiments, the reduction conditions comprise hydrogen gas in the presence of a catalyst. In some embodiments, the catalyst is sulfided 5% platinum on carbon. In some embodiments, the reaction conditions comprise a temperature of between 19° C. and 31° C., or between 21 to 31° C., or between 21 to 28° C., and a pressure of hydrogen from 20 to 40 psi, preferably 30 psi. In some embodiments, the reaction conditions comprise a solvent selected from the group consisting of methylene chloride, ethanol, methanol, and ethyl acetate. In some embodiments, the conditions comprise methylene chloride as a solvent. In some embodiments, the compound of Formula B is afforded in a yield of at least 80%. In some embodiments, the compound of Formula B is afforded in a yield of at least 85%.

In some embodiments, the compound of formula C is prepared by contacting a compound of Formula D:

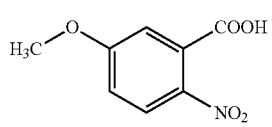

D with a compound of Formula E:

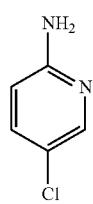

E under reaction conditions comprising to form the compound of Formula C.

In some embodiments, the reaction conditions of forming a compound of Formula II-C, for example, the compound of Formula C, comprise a temperature of between 19° C. to 31° C., or between 21 to 31° C., or between 21-28° C. In some embodiments, the reaction conditions comprise acetonitrile as a solvent. In some embodiments, the reaction conditions may further comprise other aprotic solvents in a small quantity. In some embodiments, the reaction conditions comprise phosphorous oxychloride and pyridine. In some embodiments, the reaction conditions comprise about 1 to 1.9 equivalents of phosphorous oxychloride, wherein the equivalents are based on the compound of Formula D. In a preferred embodiment, the amount of phosphorous oxychloride is less than 1.5 equivalents. In some embodiments, the amount of phosphorous oxychloride is 1.2 equivalents. In some embodiments, the compound of Formula C is afforded in a yield of at least 84%. In some embodiments, the compound of Formula C is afforded in a yield of at least 88%.

In some embodiments, the salt of Formula I or II is a pharmaceutically acceptable salt.

In some embodiments, the method of this invention further comprises contacting the compound of Formula I or II or the salt thereof with an acid under salt forming conditions to give a pharmaceutically acceptable salt of the compound of Formula I or II. In some embodiments, the method further comprises recovering the pharmaceutically acceptable salt of the compound of Formula I or II.

In some embodiments, the salt forming conditions comprise contacting a compound of Formula II, for example betrixaban, with an acid in a solvent. Compounds of Formula II, for example betrixaban, can form various salts with various organic and inorganic acids. Some examples of the salts include, but are not limited to, hydrochloric acid salt, lactate, maleate, acetate, phenoxyacetate, propionate, succinate, adipate, ascorbate, camphorate, gluconate, phosphate, tartrate, citrate, mesylate, fumarate, glycolate, naphthalene-1,5-disulfonate, gentisate, benzene sulfonate, camphor sulfonate, α-hydroxycaproate, benzoate, glucuronate, ketoglutarate, malate, malonate, mandelate, pyroglutamate, sulfate, and trans-cinnamate. One of skill in the art will recognize that other acids can be used to make salts of compounds of Formula II using the methods of the present invention. The first salt can then be converted to a second salt such as a maleate salt.

A number of methods are useful for the preparation of the salts described above and are known to those skilled in the art. For example, compounds of Formula II, such as betrixaban, may react with one or more equivalents of the desired acid in a solvent or a solvent mixture in which the salt is insoluble, or in a solvent where the solvent is removed by evaporation, distillation or freeze drying. Alternatively, compounds of Formula II, such as betrixaban, can be passed over an ion exchange resin to form the desired salt or one salt form of the product can be converted into another using the same general process.

In one embodiment, the pharmaceutically acceptable salt is maleate salt. In one embodiment, the maleate salt of betrixaban is represented by the following structure:

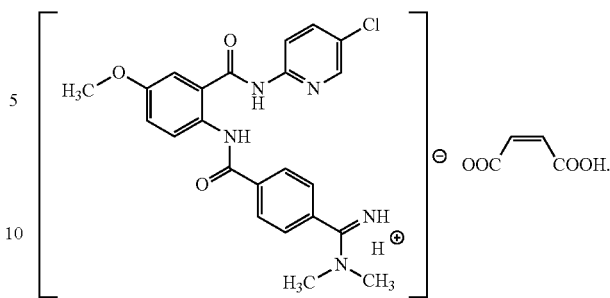

In some embodiments, the salt forming conditions comprise contacting betrixaban with at least a molar equivalent of maleic acid in a solvent mixture of $C_{1-4}$ alkanol and water at a temperature of between 10° C. and 40° C. to form the maleate salt of betrixaban.

In some embodiments, the temperature is of between 19° C. and 25° C. In one embodiment, the solvent mixture is a mixture of methanol and water. In some embodiments, the solvent mixture is a mixture of ethanol and water. In some embodiments, the solvent mixture is a mixture of methanol, ethanol and water. In some embodiments, the solvent mixture of ethanol and water is in a ratio of about 2:1 to about 8:1. In some embodiments, the solvent mixture of ethanol and water is in a ratio of about 3.5:1 to about 4.5:1. In some embodiments, the solvent mixture of ethanol and water is in a ratio of about 1:1 to 0:1.

In some embodiments, the method further comprises recovering the pharmaceutically acceptable salt of betrixaban, for example, the maleate salt of betrixaban. In one embodiment, the maleate salt is recovered from a solvent mixture of ethanol and water in a ratio of about 1:1 to 0:1. In some embodiments, the maleate salt is recovered from a solvent comprising an ethanol content and a betrixaban maleate salt content in a ratio that is lower than or equal to 6.

In some embodiments, the maleate salt of betrixaban is afforded in a yield of at least 65%. In a preferred embodiment, the maleate salt of betrixaban is afforded in a yield of at least 75%. In another preferred embodiment, the maleate salt of betrixaban is afforded in a yield of at least 85%. In another embodiment, this invention provides a method of preparing a maleate salt of betrixaban from betrixaban on a kilogram scale.

In some embodiments, this invention provides a method of preparing betrixaban which is of Formula I, or a maleate salt thereof:

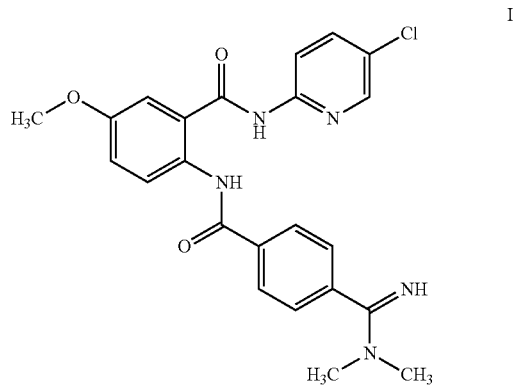

I comprising
a) contacting a compound of Formula D:

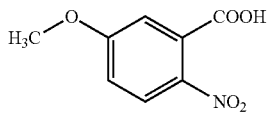

with a compound of Formula E:

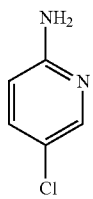

under reaction conditions optionally comprising acetonitrile as a solvent to form a compound of Formula C:

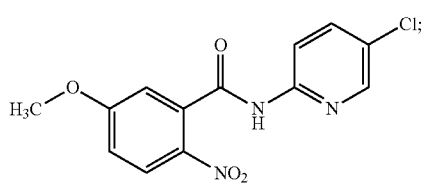

b) exposing the compound of Formula C to reduction conditions comprising hydrogen gas in the presence of a catalyst to form a compound of Formula B:

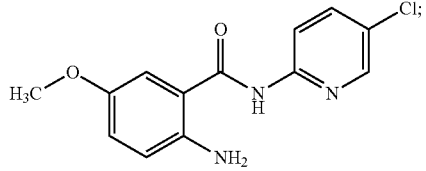

c) contacting the compound of Formula B with a compound of Formula A:

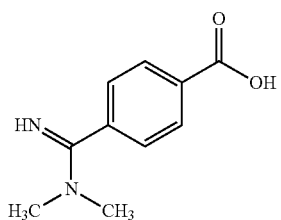

under reaction conditions comprising N-(3-dimethylaminopropyl)-N'-ethylcarbodiimide hydrochloride and optionally hydroxybenzotriazole to form betrixaban or the salt thereof; and optionally d) contacting betrixaban or the salt thereof with at least a molar equivalent of maleic acid in a solvent mixture of $C_{1-4}$ alkanol and water at a temperature of between 10° C. and 40° C. under reaction conditions to form the maleate salt of betrixaban.

The compounds employed in the methods of this invention can be prepared from readily available starting materials. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) Protecting Groups in Organic Synthesis, 3rd Edition, Wiley, New York, and references cited therein.

Furthermore, the compounds of this invention may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

The novel methods disclosed herein provide robust and cost effective processes of preparing betrixaban and its pharmaceutically acceptable salt with high purity. Methods of preparing betrixaban have been disclosed in U.S. Pat. No. 6,376,515 and WO 2008/057972, both of which are hereby incorporated by reference in their entirety. Those methods, although differing significantly in reaction types and conditions, possess the common feature of forming a cyano compound of Formula K (Step A) which is then converted to the amidine compound betrixaban (Formula I) (Step B) as outline in Scheme 1.

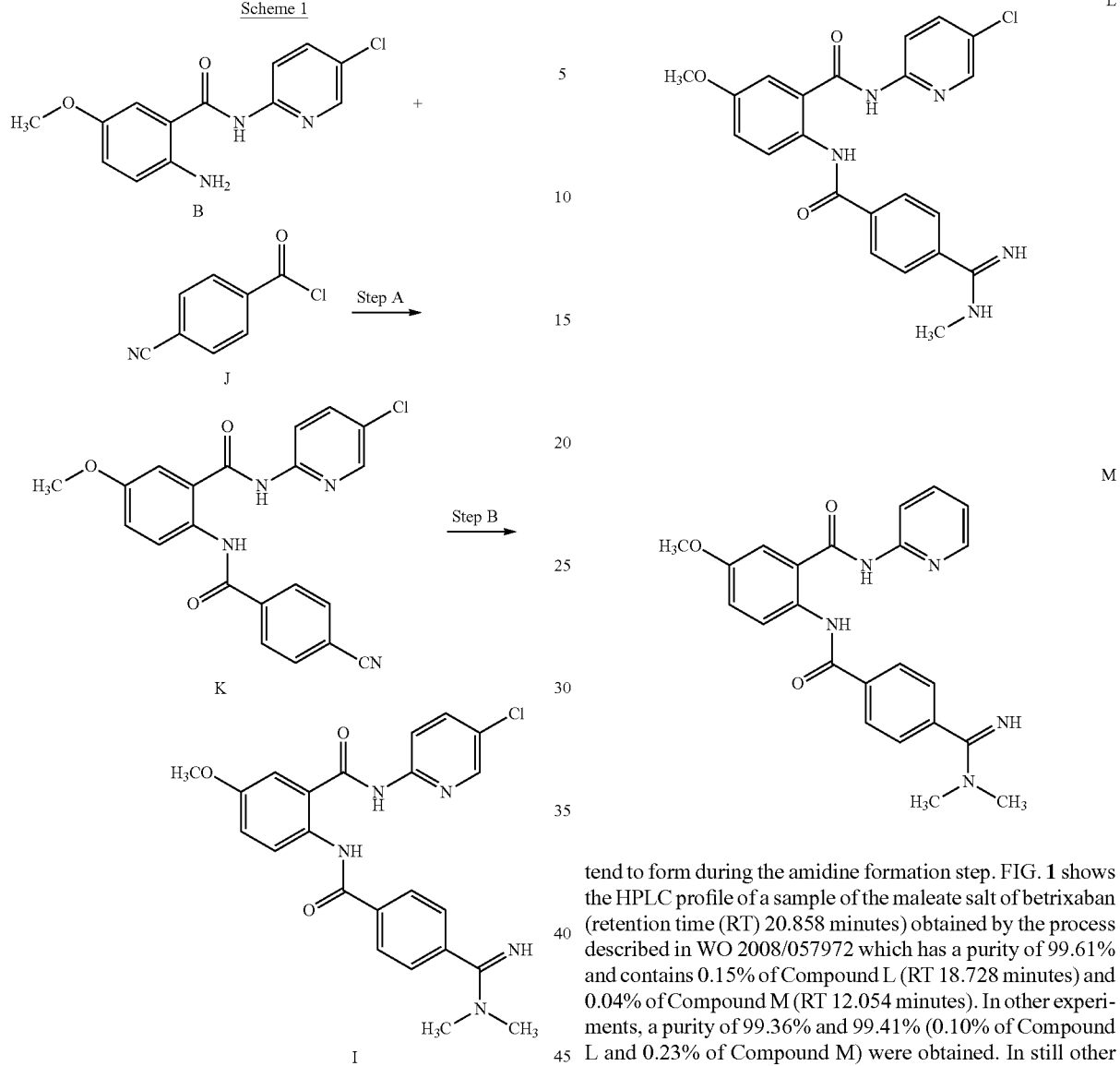

Scheme 1

In U.S. Pat. No. 6,376,515, Compound B and Compound J react in the presence of a base, such as pyridine, and a solvent, such as dichloromethane, to form Compound K in Step A. In Step B, Compound K is then converted to betrixaban via a two-step process including converting Compound K to an imidate intermediate in methanol saturated with the highly corrosive HCl gas and reacting the dried imidate intermediate with dimethyl amine in methanol under reflux conditions to give betrixaban. This process involves the use of corrosive chemicals and harsh conditions.

PCT Publication WO 2008/057972 describes an improved process of preparing betrixaban according to Scheme 1. One significant improvement is the use of a one-step process using lithium dimethylamide (formed by reaction of dimethylamine and hexyllithium) to replace the two-step process of U.S. Pat. No. 6,376,515 to convert Compound K to betrixaban. This is an efficient process which produces betrixaban with high purity in large scales under mild conditions. However, two impurities, Compounds L and M, tend to form during the amidine formation step. FIG. 1 shows the HPLC profile of a sample of the maleate salt of betrixaban (retention time (RT) 20.858 minutes) obtained by the process described in WO 2008/057972 which has a purity of 99.61% and contains 0.15% of Compound L (RT 18.728 minutes) and 0.04% of Compound M (RT 12.054 minutes). In other experiments, a purity of 99.36% and 99.41% (0.10% of Compound L and 0.23% of Compound M) were obtained. In still other experiments, about 0.06% or 0.25% of Compound M were found, and about 0.17% or about 0.25% of compound L were found. Formation of these side products affects the purity and yield of the desired product betrixaban and/or creates the need for additional purification operation. In addition, the mono-methyl Compound L is a close analogue of betrixaban and thus difficult to remove from the final product. This adversely affects the purity of betrixaban, especially for large scale preparations such as kilogram scales. Therefore the reaction conditions of the amidine formation step must be strictly controlled to minimize the formation of the two side products, Compounds L and M.

Figure 2:
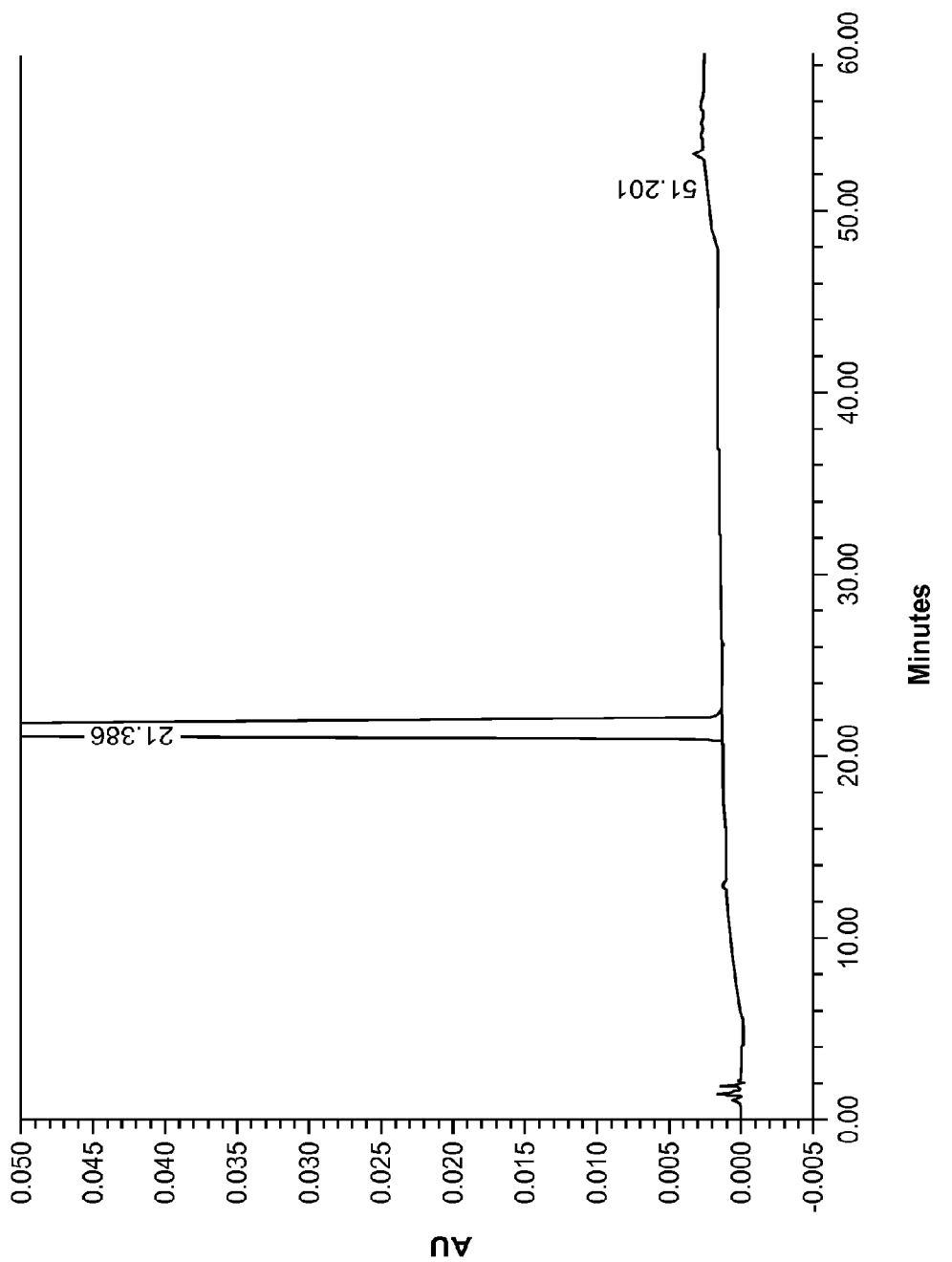
FIG. 2 provides a high performance liquid chromatography (HPLC) chromatogram of betrixaban maleate salt obtained by the method of this invention.

The methods of this invention eliminate the formation of Compound L and M without requiring stringently controlled reaction conditions, as shown in FIG. 2 and Table 1 wherein the sample prepared by the method of this invention has a purity of 99.98%. In other experiments, the purity of the betrixaban maleate salt obtained by the method of this invention ranges from 99.63% to 99.72%. Therefore the methods of this invention are more reliable and robust in producing betrixaban with improved purity and on larger scales.

TABLE 1

| | RT (minutes) | Name | Area | % Area | Height (μV) |
|---|---|---|---|---|---|
| 1 | 21.386 | Compound I | 9700078 | 99.98 | 348203 |
| 2 | 51.201 | Impurity | 1612 | 0.02 | 179 |
| Sum | | | 9701689 | | |

It is further contemplated that by employing the methods of the invention, Compounds L and M will be substantially absent from synthesis producing the free base. In fact, methods of the invention have produced betrixaban free base having a purity of at about 99.3%.

Thus, in another aspect, this invention provides substantially pure betrixaban free base and maleate salt. In one embodiment, the invention provides a composition comprising substantially pure betrixaban free base or substantially pure maleate salt. In one embodiment, the composition comprises at least about 99.3% betrixaban free base, or 99.5% betrixaban free base, or 99.7% betrixaban free base. In still other embodiments, the composition comprises at least 99.7% betrixaban maleate salt. In some embodiments, the composition comprises at least 99.8% betrixaban maleate salt. In some embodiments, the composition comprises at least 99.9% betrixaban maleate salt.

In still another aspect, this invention provides a composition comprising betrixaban free base or maleate salt that is substantially free of Compound L and/or Compound M. In some embodiments, the composition is free of Compound M and substantially free of Compound L. In some embodiments, the composition is free of Compound L and substantially free of Compound M. In some embodiments, the composition comprising betrixaban free base or maleate salt that is free of Compound L and/or Compound M.

In still another aspect, this invention provides a composition comprising at least 99.3% betrixaban free base, which composition is obtainable by the methods of this invention. In some embodiments, the composition having at least 99.3% betrixaban free base is obtainable by (1) contacting a compound of Formula A with a compound of Formula B under reaction conditions to form betrixaban or a salt thereof; and (2) recovering betrixaban free base obtained in (1) with a purity of equal to or greater than 99.3%. In some embodiments, the composition comprises at least 99.5% betrixaban free base. In some embodiments, the composition comprises at least 99.7% betrixaban free base.

In still another aspect, this invention provides a composition comprising at least 99.7% betrixaban maleate salt, which composition is obtainable by the methods of this invention. In some embodiments, the composition having at least 99.7% betrixaban maleate salt is obtainable by (1) contacting a compound of Formula A with a compound of Formula B under reaction conditions to form betrixaban or a salt thereof; (2) contacting betrixaban or the salt thereof obtained in (1) with maleic acid under salt forming conditions to form betrixaban maleate salt, and (3) recovering betrixaban maleate salt obtained in (2) with a purity of equal to or greater than 99.7%. In some embodiments, the composition comprises at least 99.8% betrixaban maleate salt. In some embodiments, the composition comprises at least 99.9% betrixaban maleate salt.

III. Use of the Compounds

The compounds and/or salts prepared by the present invention can be used for commercial synthesis or for preventing or treating a condition in a mammal characterized by undesired thrombosis by administering to the mammal a therapeutically effective amount of a compound of Formula II, for example betrixaban, or a pharmaceutically acceptable salt thereof, for example the maleate salt of betrixaban. The compound of Formula II or a pharmaceutically acceptable salt thereof can be used either alone or in conjunction with pharmaceutically acceptable excipients to prevent the onset of a condition characterized by undesired thrombosis. The compounds and/or salts prepared the present invention can also be used either alone or in conjunction with pharmaceutically acceptable excipients as prophylactic treatment for patients where the condition is not detected sufficiently early to prevent onset.

The compounds of Formula II, for example betrixaban, or a pharmaceutically acceptable salt thereof, are characterized by their ability to inhibit thrombus formation with acceptable effects on classical measures of coagulation parameters, platelets and platelet function, and acceptable levels of bleeding complications associated with their use. Conditions characterized by undesired thrombosis would include those involving the arterial and venous vasculature.

The compounds and/or salts prepared by the present invention are useful in treating thrombosis and conditions associated with thrombosis. The compounds or salts prepared by the present invention, selected and used as disclosed herein, are believed to be useful for preventing or treating a condition characterized by undesired thrombosis, such as (a) the treatment or prevention of any thrombotically mediated acute coronary syndrome including myocardial infarction, unstable angina, refractory angina, occlusive coronary thrombus occurring post-thrombolytic therapy or post-coronary angioplasty, (b) the treatment or prevention of any thrombotically mediated cerebrovascular syndrome including embolic stroke, thrombotic stroke or transient ischemic attacks, (c) the treatment or prevention of any thrombotic syndrome occurring in the venous system including deep venous thrombosis or pulmonary embolus occurring either spontaneously or in the setting of malignancy, surgery or trauma, (d) the treatment or prevention of any coagulopathy including disseminated intravascular coagulation (including the setting of septic shock or other infection, surgery, pregnancy, trauma or malignancy and whether associated with multi-organ failure or not), thrombotic thrombocytopenic purpura, thromboangiitis obliterans, or thrombotic disease associated with heparin induced thrombocytopenia, (e) the treatment or prevention of thrombotic complications associated with extracorporeal circulation (e.g. renal dialysis, cardiopulmonary bypass or other oxygenation procedure, plasmapheresis), (f) the treatment or prevention of thrombotic complications associated with instrumentation (e.g. cardiac or other intravascular catheterization, intra-aortic balloon pump, coronary stent or cardiac valve), and (g) those involved with the fitting of prosthetic devices.

In some embodiments, compounds and/or a pharmaceutically acceptable salt thereof prepared by this invention are useful in: prevention of stroke in atrial fibrillation patients; prevention of thrombosis in medically ill patients; prevention and treatment of deep vein thrombosis; prevention of arterial thrombosis in acute coronary syndrome patients; and/or secondary prevention of myocardial infarction, stroke or other thrombotic events in patients who have had a prior event.

The compound of Formula II, for example betrixaban, or a pharmaceutically acceptable salt thereof, for example, the maleate salt of betrixaban, can also be used whenever inhibition of blood coagulation is required such as to prevent coagulation of stored whole blood and to prevent coagulation in other biological samples for testing or storage. Thus coagulation inhibitors prepared by this invention can be added to or contacted with stored whole blood and any medium containing or suspected of containing plasma coagulation factors and in which it is desired that blood coagulation be inhibited, e.g. when contacting the mammal's blood with material selected from the group consisting of vascular grafts, stents, orthopedic prosthesis, cardiac prosthesis, and extracorporeal circulation systems.

Besides being useful for human treatment, these compounds and/or salts are also useful for veterinary treatment of companion animals, exotic animals and farm animals, including mammals, rodents, and the like. More preferred animals include horses, dogs, and cats.

IV. Examples

Unless stated otherwise, the abbreviations used throughout the specification have the following meanings.

A %=total percent area
aq.=aqueous
cm=centimeter
con=concentrated
d=doublet
DCM=dichloromethane
EDC=N-(3-dimethylaminopropyl)-N'-ethylcarbodiimide
EDTA=ethylenediaminetetraacetic acid
eq. equivalent
EtOH=ethanol
g=gram
HPLC=high performance liquid chromatography
hr=hour
Hz=hertz
IR=infrared
J=coupling constant
kg=kilogram
L=liter
LOD=limit of detection
M=molar
m=multiplet
Me=methyl
MeO=methoxy
MeOH=methanol
mg=milligram
min.=minute
mL=milliliter
mm=millimeter
MTBE=methyl tert butyl ether
N=Normal
nM=nanomolar
NMR=nuclear magnetic resonance
psi=Pounds per square inch
s=singlet
TDS=total dissolved solids
THF=tetrahydrofuran
v/w=Volume by weight
μM=micromolar

Example 1

Preparation of Betrixaban

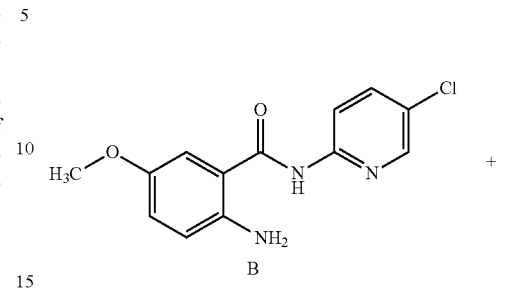

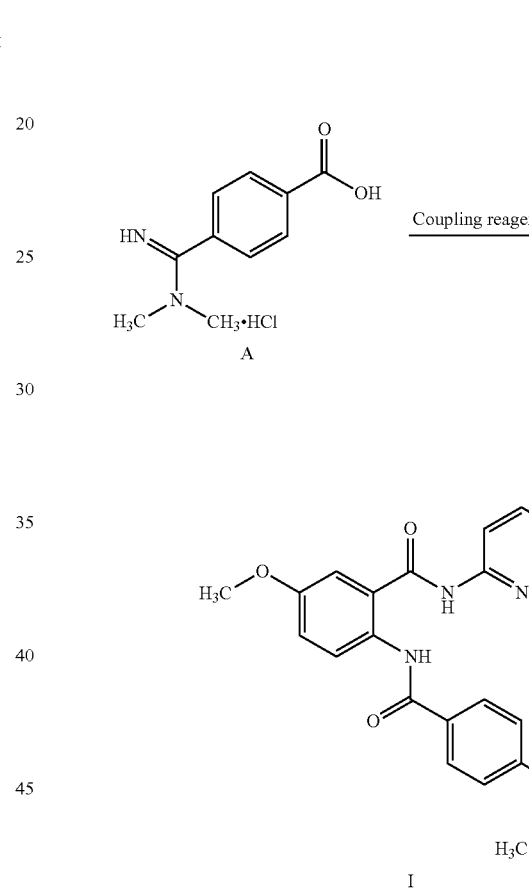

Dimethylformamide (13 L) and hydrochloride (18 mL) were charged into a reactor. Compound B (1 kg) was added followed by Compound A (0.88 kg). Compound A is commercially available or, just as with Compound B may be prepared using the methods described in Examples 4 and 5. The reaction mixture was cooled between 0° C. and −10° C. EDC (0.752 kg) was added while maintaining the temperature between −10° C. and 0° C. The reaction mixture was stirred until the content of Compound B is below 0.10% area by HPLC. The reaction mixture was stirred until betrixaban started to crystallize. Acetone (26 L) was then added during a period of at least 1 hr while the temperature was maintained at between −10° C. and 0° C. The suspension was then stirred for additional 2 hrs at a temperature of between 0° C. and 10° C. The suspension was filtered and washed with cold acetone to give a wet product betrixaban.

Example 2

Preparation of a Maleate Salt of Betrixaban

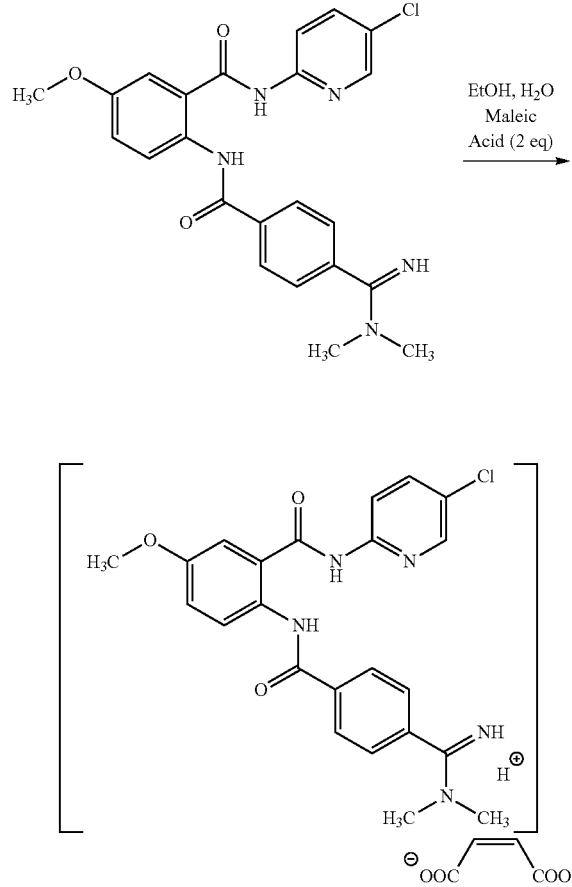

Figure 3:
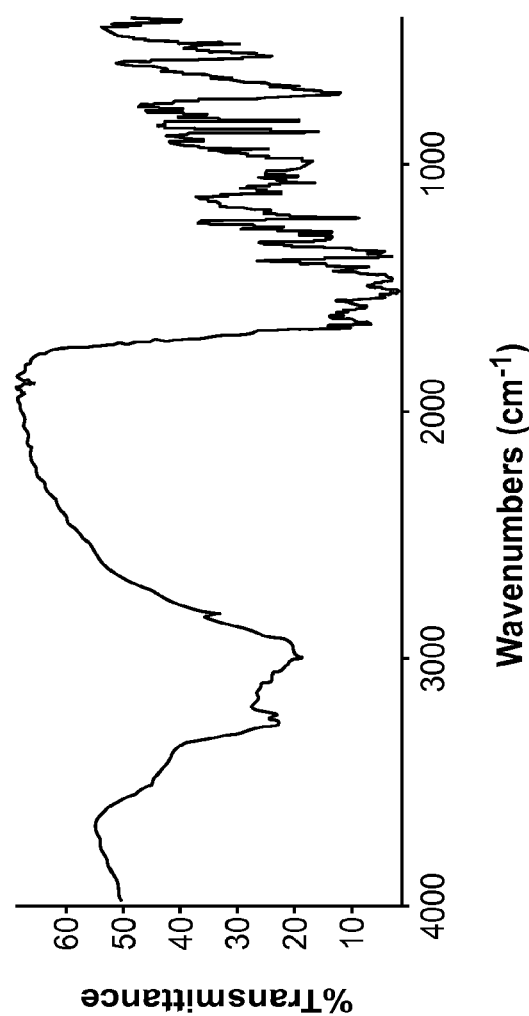
FIG. 3 provides an infra red (IR) spectrum of betrixaban maleate salt obtained by the method of this invention.
Figure 4:
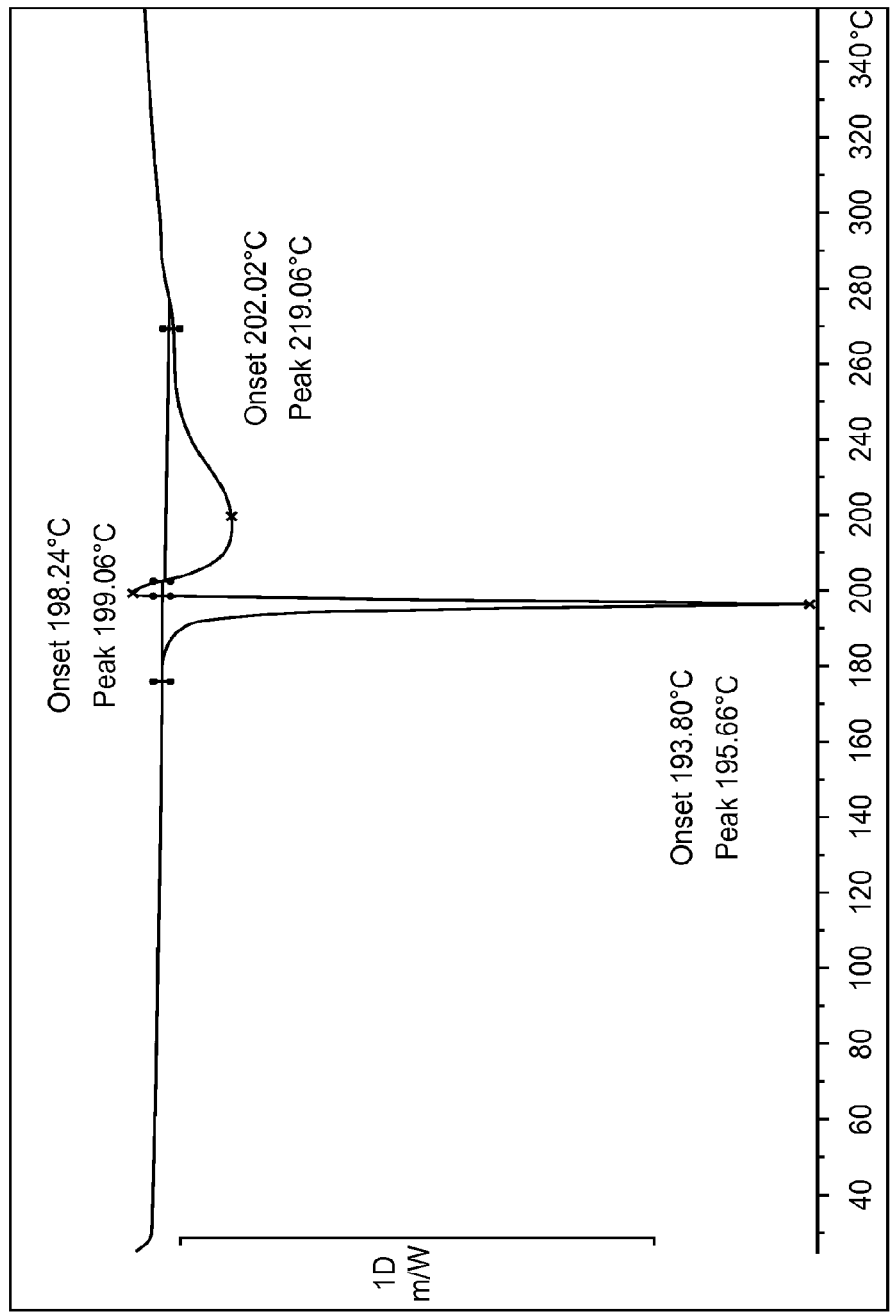
FIG. 4 provides a differential scanning calorimetry (DSC) of betrixaban maleate salt obtained by the method of this invention.
Figure 5:
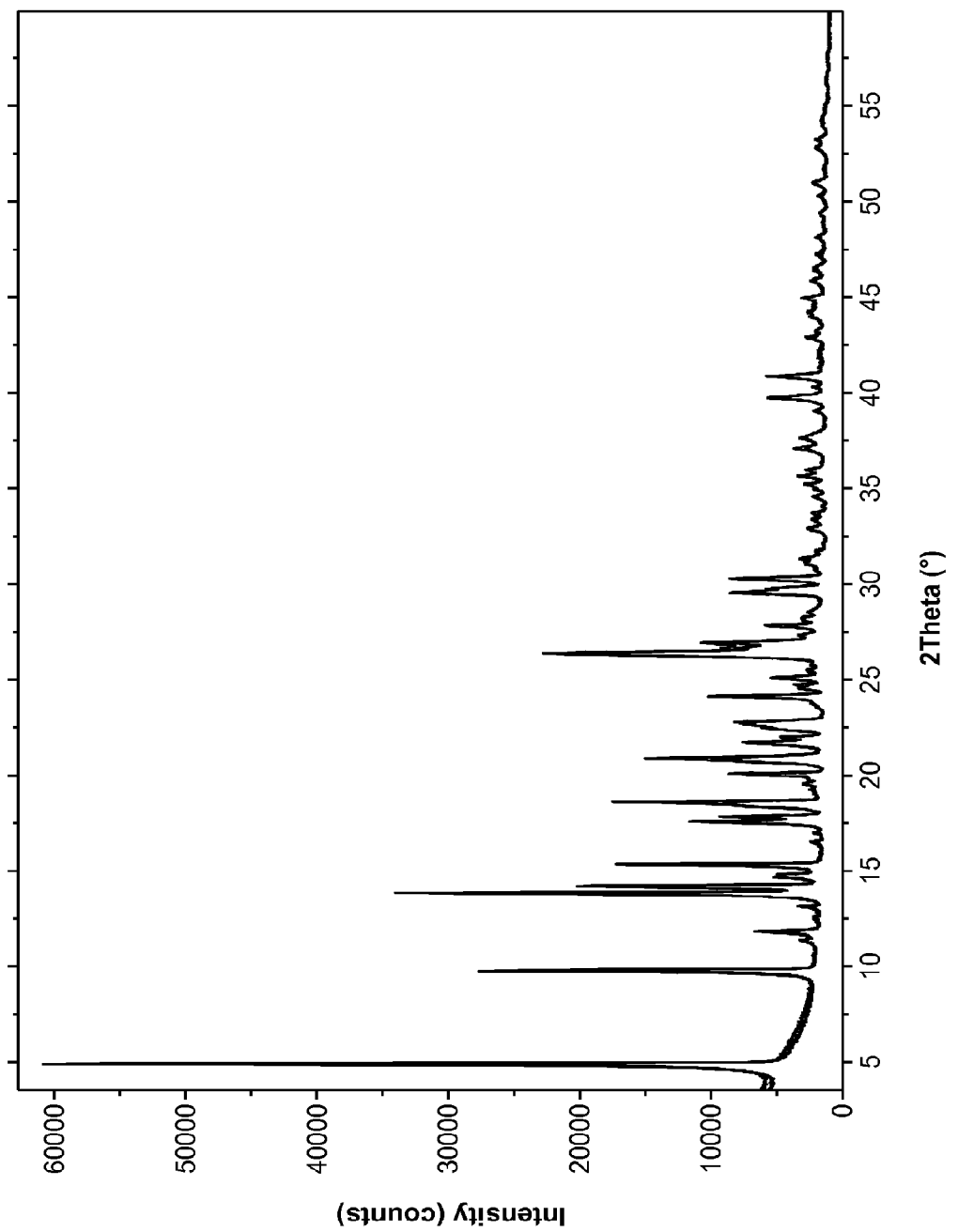
FIG. 5 provides an overlay of the X-ray powder diffraction (XRPD) patterns of betrixaban maleate salt obtained by the method of this invention and of the reference standard obtained by the method described in Scheme 1.

The wet betrixaban obtained above was reacted with maleic acid (0.52×weight of maleic acid/weight of dry betrixaban) in ethanol (22.4× volume of liquid/weight of dry betrixaban (v/w)) and purified water (5.7×v/w)) to form a betrixaban maleate salt. The solution of the betrixaban maleate salt was filtered and concentrated under vacuum until a final volume of 5.7×v/w. Water (2×v/w) was then added and the mixture was back concentrated until the same volume. The procedure of adding water and distil until a final volume of 5.7×v/w was carried out until the molar ratio between the content of ethanol and the content of betrixaban maleate salt in the mixture was lower than, or equal to, 6. Betrixaban maleate salt crystallized during the removal of ethanol. The suspension was cooled to a temperature between 19° C. and 25° C. and stirred for not less than 2 hours at this temperature range. Betrixaban maleate salt was isolated by filtration, washed with water and dried under vacuum at a maximum temperature of 40° C. until the content of water was lower than, or equal to, 0.5% w/w by Karl-Fisher. The purity of the maleate salt was determined to be greater than 99% by HPLC. The betrixaban maleate isolated was in a crystalline form A which was concluded based on IR, DSC and XRPD results obtained, see FIGS. 3-5, respectively. The major peaks of XRPD pattern of crystalline form A are also listed in Table 2.

TABLE 2

| Betrixaban Form A XRPD Peak °2-Theta(2θ°) | |
|---|---|
| Angle (°2-Theta) | Intensity (%) |
| 5.02 | 100.0 |
| 10.01 | 45 |
| 13.89 | 30 |
| 14.02 | 20 |
| 15.02 | 10 |
| 17.5 | 10 |
| 18.02 | 10 |
| 20.02 | 5 |
| 26.5 | 30 |

Example 3

Synthesis of 2-nitro-N-(5-chloro-pyridin-2-yl)-5-methoxy-benzamide (C)

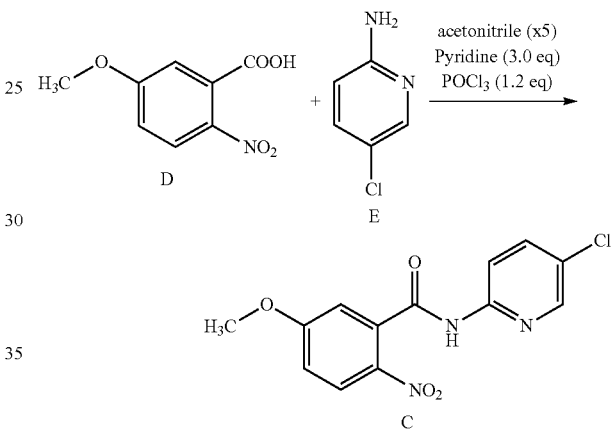

5-Methoxy-2-nitrobenzoic acid (D) (25.0 kg, 1.0 eq.), 2-amino-5-chloropyridine (E) (16.3 kg, 1.0 eq.), and acetonitrile (87.5 kg) were charged to a 380 L glass-lined reactor. The reaction mixture was adjusted to 22° C. (19-25° C.) and anhydrous pyridine (30.0 kg, 3.0 eq.) was added. The pump and lines were rinsed forward with acetonitrile (22.5 kg), and the reactor contents were adjusted to a temperature of 19-22° C. Phosphorous oxychloride (23.3 kg, 1.20 eq.) was charged to the contents of the reactor via a metering pump, while maintaining a temperature of 25° C. (22-28° C.). The metering pump and lines were rinsed forward with acetonitrile (12.5 kg), while keeping the temperature at 25° C. (22-28° C.). The reaction mixture normally turned from a slurry to a clear solution after the addition of about ⅓ of the POCl₃. At the end of the addition, it became turbid. After complete addition, the reaction mixture was agitated at 25° C. (22-28° C.) for ca. 1 hr, at which time HPLC analysis confirmed reaction completion. The solution was cooled to 15° C. (12-18° C.) and water (156.3 kg) was charged slowly while keeping reaction temperature of between 12 and 30° C. The reaction mixture was then adjusted to 22° C. (19-25° C.) and agitated for ca. 5 hrs until exotherm ceased. Formation of a slurry was visually confirmed and the contents of the reactor were filtered onto a pressure nutsche fitted with a filter cloth. The reactor, pump, and lines were washed forward onto the pressure nutsche with two portions of water (62.5 kg). The filtrate had a pH value of 7. The product (41.8 kg) was dried under vacuum with a maximum temperature of water bath (to heat dryer jacket) of 50° C. After ca. 12 hrs, in-process LOD analysis indicated a solvent content of 0.72%. The dry product (C) was discharged (34.4 kg) with 88.2% yield and 99.1% purity by HPLC.

Example 4

Synthesis of 2-amino-N-(5-chloro-pyridin-2-yl)-5-methoxy-benzamide (B)

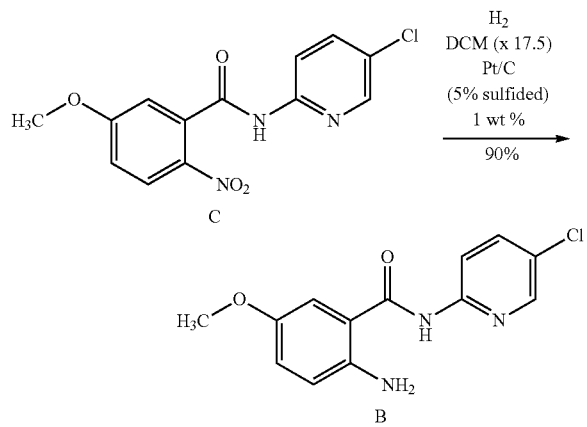

Process A

To a 780 L Hastelloy reactor, Compound C (33 kg, 1.0 eq.), 5% platinum carbon (sulfided, 0.33 kg) and dichloromethane (578 kg) were charged. Agitation was started and reactor contents were adjusted to 22° C. (19-25° C.). The reactor was pressurized with ca. 30 psi hydrogen and the reaction mixture gently heated to 28° C. (25-31° C.). Hydrogenation of the reactor contents was performed under ca. 30 psi at 28° C. (25 to 31° C.; maximum 31° C.) until the reaction was complete by HPLC. After 16.5 hrs, the reaction was deemed complete after confirming the disappearance of starting material (0.472 A %). The contents of the reactor were circulated through a conditioned Celite™ (diatomaceous earth; Celite Co., Santa Barbara, Calif.) pad (0.2-0.5 kg Celite™ conditioned with 20-55 kg dichloromethane) prepared in a 8" sparkler filter to remove the platinum catalyst. The reactor and Celite™ bed were rinsed forward with two portions of dichloromethane (83 kg). The filtrate was transferred to and concentrated in a 570 L glass-lined reactor under an atmospheric pressure to ca. 132 L. Ethanol (69 kg) was charged and concentration continued under atmospheric pressure to ca. 99 L. In-process NMR indicated that the dichloromethane content was 39%. Ethanol (69 kg) was charged again and concentration continued again to ca. 99 L. In-process NMR indicated that the dichloromethane content was 5%. The reaction mixture was then adjusted to 3° C. (0 to 6° C.), agitated for ca. 1 hr, and the resulting slurry filtered onto a jacketed pressure nutsche fitted with a filter cloth. The reactor, pump, and lines were rinsed forward with cold [3° C. (0-6° C.)]ethanol (26 kg. The wet filter cake (36.6 kg) was dried under vacuum at 40-50° C. with a maximum temperature of water bath (to heat dryer jacket) of 50° C. LOD analysis after 12.5 hrs indicated solvent content was at 0.1%. The dry product (B) was discharged (26.4 kg) in 89.5% yield. HPLC showed 98.4 A % purity, with dechlorinated impurity at 0.083%.

Process B

To a 780 L Hastelloy reactor, Compound C (33 kg, 1.0 eq.), 5% platinum carbon (sulfided, 0.33 kg) and dichloromethane (578 kg) were charged. Agitation was started and reactor contents were adjusted to 22° C. (19-25° C.). The reactor was pressurized with ca. 30 psi hydrogen and the reaction mixture gently heated to 26° C. (21 to 31° C.). Hydrogenation of the reactor contents was performed under ca. 30 psi at 26° C. (21 to 31° C.; maximum 31° C.) until the reaction was complete by HPLC. After 16.5 hrs, the reaction was deemed complete after confirming the disappearance of starting material (0.472 A %). The contents of the reactor were circulated through a conditioned Celite™ pad (0.2-0.5 kg Celite™ conditioned with 20-55 kg dichloromethane) prepared in a 8" sparkler filter to remove the platinum catalyst. The reactor and Celite™ bed were rinsed forward with two portions of dichloromethane (83 kg). The filtrate was transferred to and concentrated in a 570 L glass-lined reactor under vacuum and a maximum temperature of 45° C. to ca. 132 L. Ethanol (69 kg) was charged and concentration continued under vacuum and a maximum temperature of 45° C. to ca. 132 L. In-process NMR indicated that the dichloromethane content was 39%. Ethanol (69 kg) was charged again and concentration continued again to ca. 132 L. In-process NMR indicated that the dichloromethane content was 5%. The reaction mixture was then adjusted to 3° C. (0 to 6° C.), agitated for ca. 1 hr, and the resulting slurry filtered onto a jacketed pressure nutsche fitted with a filter cloth. The reactor, pump, and lines were rinsed forward with cold [3° C. (0-6° C.)]ethanol (26 kg. The wet filter cake (36.6 kg) was dried under vacuum at 40-50° C. with a maximum temperature of water bath (to heat dryer jacket) of 50° C. LOD analysis after 12.5 hrs indicated solvent content was at 0.1%. The dry product (B) was discharged (26.4 kg) in 89.5% yield. HPLC showed 98.4 A % purity, with dechlorinated impurity at 0.083%.

Example 5

Synthesis of 4-(N,N-dimethylcarbamimidoyl)benzoic acid (A)

Process A

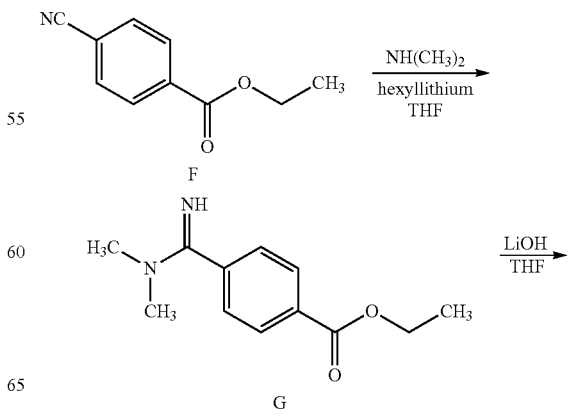

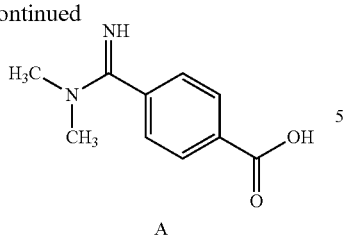

A

Step 1: Amidine Formation

To a tetrahydrofuran solution of 2M dimethylamine, 2.3M hexane solution of hexyllithium was slowly added over a period of at least three (3) hours while maintaining the temperature at between −8° C. and −12° C. This solution was added to the tetrahydrofuran solution of ethyl-4-cyanobenzoate (F) while maintaining the temperature between −8° C. and −12° C. The completion of the reaction was confirmed by HPLC, and the solution temperature was adjusted to between −8° C. and 3° C. The reaction mixture was slowly added to the cold solution of aqueous sodium bicarbonate solution and the desired ethyl-4-(N,N-dimethylcarbamimidoyl)benzoate (G) was extracted with ethyl acetate. The ethyl acetate layer was dried, filtered and evaporated under vacuum to afford ethyl-4-(N,N-dimethylcarbamimidoyl)benzoate (G) as a white solid.

Step 2: Hydrolysis of Ester

To a THF solution of ethyl-4(N,N-dimethylcarbamimidoyl)benzoate (G) was added an aqueous solution of lithium hydroxide (2 eq.) and the reaction mixture was stirred for 6 hr. The completion of the reaction was confirmed by HPLC. To the reaction mixture was added water, followed by extraction with ethyl acetate. The aqueous layer was acidified with 6N HCl to pH between 3-4 at which point the desired 4-(N,N-dimethylcarbamimidoyl)benzoic acid precipitated as the white solid. The white solid isolated was washed with hexane to afford 4-(N,N-dimethylcarbamimidoyl)benzoic acid as an hydrochloride salt (A).

Process B

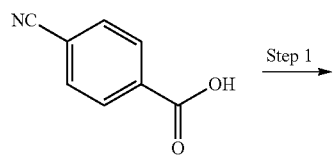

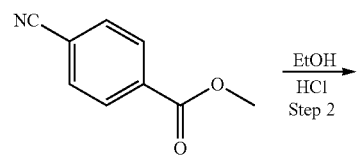

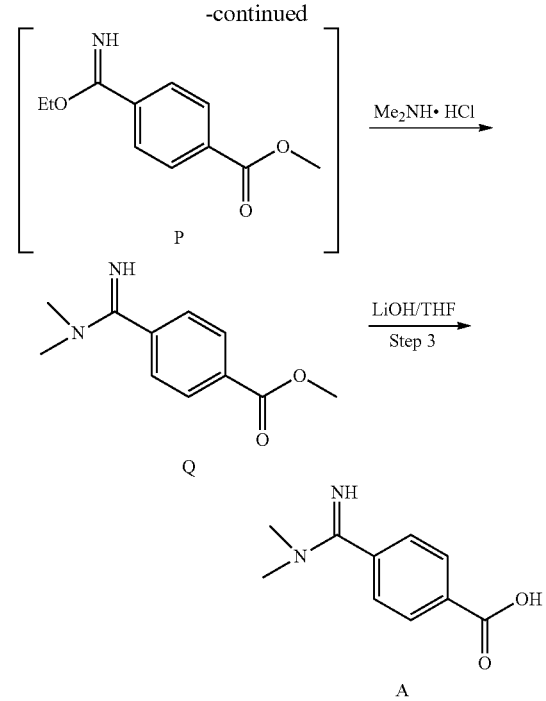

Step 1: Ester Formation

To a methanolic solution of 4-cyanobenzoic acid was added concentrated sulfuric acid and refluxed the reaction for at least 12 hours. The completion of the reaction was confirmed by HPLC. The solution was cooled and the solvent was evaporated. To the residue was added ethyl acetate followed by washing with 10% sodium hydroxide solution. The ethyl acetate layer was dried, filtered and evaporated to give desired 4-methyl cyanobenzoate as a white solid.

Step 2: Dimethylamidine Formation

A stream of HCl (gas) was bubbled through a 0° C. solution of 4-methyl cyanobenzoate (1 mmol) in 50 mL of ethanol until saturation. The mixture was stirred at room temperature overnight and evaporated to afford compound P. The resulting residue was treated with dimethylamine hydrochloride (0.15 eq.) in 20 mL ethanol at reflux temperature for 4 hours. The solvent was removed at reduced pressure and the residue was washed with hexane to afford desired product Q as a light yellow solid.

Step 3: Ester Hydrolysis

To a THF solution of ethyl-4(N,N-dimethylcarbamimidoyl)benzoate (Q) was added an aqueous solution of lithium hydroxide (2 eq.) and the reaction mixture was stirred for 6 hours. The completion of the reaction was confirmed by HPLC. To the reaction mixture was added water, followed by extraction with ethyl acetate. The aqueous layer was acidified with 6N HCl to pH between 3-4 at which point the desired 4-(N,N-dimethylcarbamimidoyl)benzoic acid precipitated as the white solid. The white solid isolated was washed with hexane to afford 4-(N,N-dimethylcarbamimidoyl)benzoic acid as an hydrochloride salt (A).

Example 6

Preparation of Betrixaban, Free Base

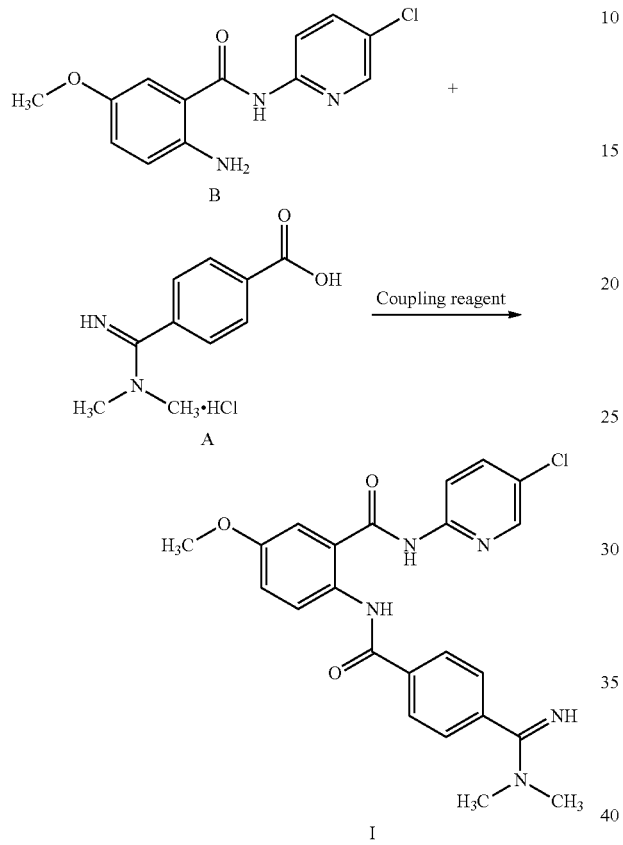

To 100 mL round bottom flask, was added compound B (2.0 g, obtained as in Example 4), compound A (1.98 g, obtained as in example 5), 20 mL N,N-dimethylacetamide. The reaction mixture was stirred briefly so as to dissolve most of the solid, then con. HCl (36 microliters) was added. To this thin slurry add EDC.HCl (1.8 g total, Aldrich) in 3 portions, 0.6 g each, 20 min apart. The reaction mixture was stirred for 1.5 hours for complete reaction.

To this reaction was added 2.3 g sodium carbonate solution in 10 mL water while the batch was cooled with water bath to keep the batch temperature 22-30° C. Vigorous agitation was required to keep the batch well mixed. Then 10 mL water was added. The batch was stirred at 22-25° C. for 30 min. After a slurry was formed, 20 mL more water was added. The batch was stirred at 22° C. for 1 hour. The batch was filtered and the wet cake was washed with 3×5 mL water, then 5 mL acetone. The cake was dried on the funnel by suction. The weight of the dry cake is 2.95 g-2.92 g which is the crude betrixaban. To purify the crude betrixaban obtained, 1.0 g of the crude solid was mixed with 4 mL N,N-dimethylacetamide and heated to 70° C. for 30 min. Then add 8 mL toluene was added and the mixture was heated for 30 min, then cooled to 22° C. over 1 h, then cooled to 0° C., aged at 0° C. for 2 hours, filtered, washed with 2×1 mL toluene. The cake was dried on the funnel by suction to obtain 0.88 g pure betrixaban (I).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A composition comprising at least 99.7% betrixaban free base or at least 99.7% betrixaban maleate salt.

2. The composition of claim 1, comprising at least 99.8% betrixaban maleate salt.

3. The composition of claim 2, comprising at least 99.9% betrixaban maleate salt.

4. A composition comprising betrixaban free base or salt thereof that comprises less than 0.15% of Compound L and/or Compound M:

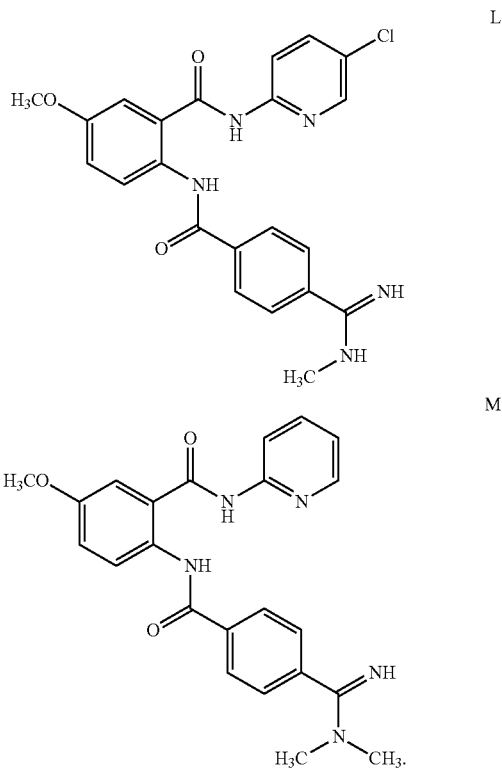

5. The composition of claim 4 wherein the salt is the maleate salt.

* * * * *